(12) United States Patent
Sundermann et al.

(10) Patent No.: US 7,776,848 B2
(45) Date of Patent: Aug. 17, 2010

(54) SPIROCYCLIC CYCLOHEXANE COMPOUNDS

(75) Inventors: Bernd Sundermann, Aachen (DE); Claudia Hinze, Aachen (DE); Hans Schick, Berlin (DE); Helmut Sonnenschein, Berlin (DE)

(73) Assignee: Gruenenthal GmbH, Aachen (DE)

( * ) Notice: Subject to any disclaimer, the term of this patent is extended or adjusted under 35 U.S.C. 154(b) by 222 days.

(21) Appl. No.: 11/705,096

(22) Filed: Feb. 12, 2007

(65) Prior Publication Data

US 2007/0213351 A1 Sep. 13, 2007

Related U.S. Application Data

(63) Continuation of application No. PCT/EP2005/008625, filed on Aug. 9, 2005.

(30) Foreign Application Priority Data

Aug. 13, 2004 (DE) ........................ 10 2004 039 382

(51) Int. Cl.
*A01N 43/42* (2006.01)
(52) U.S. Cl. ...................... 514/183; 514/278
(58) Field of Classification Search ........................ None
See application file for complete search history.

(56) References Cited

U.S. PATENT DOCUMENTS

2006/0004034 A1* 1/2006 Hinze et al. ................. 514/278

FOREIGN PATENT DOCUMENTS

| CA | 2423935 | * | 3/2007 |
|---|---|---|---|
| EP | 0 466 548 A1 | | 1/1992 |
| EP | 1 142 587 A1 | | 10/2001 |
| NL | 6512087 | | 3/1966 |
| WO | WO 99/64420 | | 12/1999 |
| WO | WO 02/30870 | * | 3/2003 |
| WO | WO 2004/043967 | * | 5/2004 |
| WO | WO 2004/043967 A1 | | 5/2004 |
| WO | WO 2004/113336 A1 | | 12/2004 |
| WO | WO 2005/033112 A2 | | 4/2006 |

OTHER PUBLICATIONS

Wermuth (The Practice of Medicinal Chemistry, Chapter 13:Molecular variations based on isosteric replacements, 1996).*
Flick et al (Arzneimittel-Forschung 28(1A):107-113, 1978) Abstract Only.*
International Search Report dated Jan. 27, 2006 with English translation of pertinent portion (Five (5) pages).
German Search Report dated Sep. 26, 2005 with English translation of pertinent portion (Eight (8) pages).
Form PCT/IB/373, PCT/ISA/237 International Preliminary Report on Patentability dated Jan. 2004 (Eight (8) pages).
E. Morelli et al., Specific Targeting of Peripheral Serotonin 5-$HT_3$ Receptors. Synthesis, Biological Investigation, and Structure-Activity Relationships, *J. Med. Chem.* 2009, 52, pp. 3548-3562.
M. Yu et al., Identification of piperazine-bisamide GHSR antagonists for the treatment of obesity. *Bioorg. Med. Chem. Lett.* 20 (2010), pp. 1758-1762.

* cited by examiner

*Primary Examiner*—Brandon J Fetterolf
*Assistant Examiner*—Craig Ricci
(74) *Attorney, Agent, or Firm*—Crowell & Moring LLP

(57) ABSTRACT

Spirocyclic cyclohexane compounds, methods for their preparation, pharmaceutical compositions containing such compounds, and the use of such compounds to treat and/or inhibit specific undesirable conditions in a patient.

22 Claims, No Drawings

SPIROCYCLIC CYCLOHEXANE COMPOUNDS

CROSS REFERENCE TO RELATED APPLICATIONS

This application is a continuation of international patent application no. PCT/EP2005/008625, filed Aug. 9, 2005 designating the United States of America and published in German on Feb. 23, 2006 as WO 2006/018184, the entire disclosure of which is incorporated herein by reference. Priority is claimed based on Federal Republic of Germany patent application no. DE 10 2004 039 382.6, filed Aug. 13, 2004.

BACKGROUND OF THE INVENTION

The present invention relates to spirocyclic cyclohexane compounds, to processes for their preparation, to medicaments containing these compounds, and to the use of spirocyclic cyclohexane compounds in the preparation of medicaments.

The treatment of chronic and non-chronic pain is of great importance in medicine. There is a worldwide need for highly effective therapies for pain. The urgent need for action in respect of a specific treatment for chronic and non-chronic pain that is fair to the patient, which is to be understood as meaning the successful and satisfactory treatment of pain for the patient, is documented in the large number of scientific works that have appeared recently in the field of applied analgesia or fundamental research into nociception.

Conventional opioids such as morphine are highly effective in the therapy of severe to very severe pain. However, their use is limited by the known side-effects, for example respiratory depression, vomiting, sedation, constipation and the development of tolerance. In addition, they are less effective in cases of neuropathic or incidental pain, from which tumour patients in particular suffer.

Aminomethylcyclohexane derivatives for the treatment of pain are already known from the literature: WO 0230870 describes substituted C-cyclohexylmethylamine derivatives which are suitable for the treatment of pain. These compounds are likewise substituted at the 4-position of the cyclohexane ring but are still linked to the corresponding radical via a single or double bond and do not form a spirocyclic compound with the cyclohexane ring.

SUMMARY OF THE INVENTION

Accordingly, it was an object of the present invention to provide new pharmacologically active compounds;

Another object of the invention was to provide pharmaceutically active compounds and compositions that act on the opioid receptor system.

A further object of the invention was to provide pharmaceutically active compounds and compositions that are suitable for treating and/or inhibiting various diseases associated with the opioid receptor system.

An additional object of the invention was to provide new methods of treating various undesirable conditions mediated through the opioid receptor system in a patient.

The invention accordingly provides spirocyclic cyclohexane compounds corresponding to formula I:

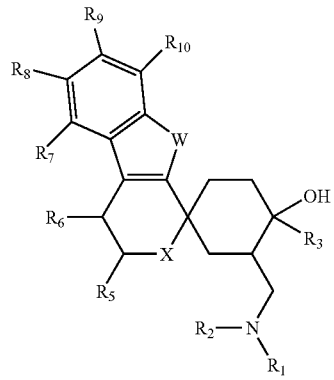

wherein
$R^1$ and $R^2$ independently of one another represent H; CHO; $C_{1-5}$-alkyl, in each case saturated or unsaturated, branched or unbranched, mono- or poly-substituted or unsubstituted; or aryl, $C_{3-8}$-cycloalkyl or heteroaryl bonded via $C_{1-3}$-alkyl, in each case mono- or poly-substituted or unsubstituted; or
$R^1$ and $R^2$ together represent $CH_2CH_2OCH_2CH_2$, $CH_2CH_2NR^{11}CH_2CH_2$ or $(CH_2)_{3-6}$, wherein
  $R^{11}$ represents H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;
$R^3$ represents phenyl, phenethyl, thiophenyl, pyridyl or benzyl, in each case unsubstituted or mono- or poly-substituted;
W represents $NR^4$, O or S;
$R^4$ represents H; $C_{1-5}$-alkyl, saturated or unsaturated, branched or unbranched, unsubstituted or mono- or poly-substituted; aryl or heteroaryl, in each case substituted or unsubstituted; aryl, heteroaryl or cycloalkyl bonded via a $C_{1-3}$-alkyl group, in each case mono- or poly-substituted or unsubstituted; $COR^{12}$; $SO_2R^{12}$, wherein
  $R^{12}$ represents H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted; $OR^{13}$; $NR^{14}R^{15}$;
$R^5$ represents =O; H; $COOR^{13}$, $CONR^{13}$, $OR^{13}$; $C_{1-5}$-alkyl, saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted;
$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted; or $R^5$ and $R^6$ together represent $(CH_2)_n$ wherein n=2, 3, 4, 5 or 6, wherein individual hydrogen atoms can also be replaced by F, Cl, Br, I, $NO_2$, $CF_3$, $OR^{13}$, CN or $C_{1-5}$-alkyl;

$R^7$, $R^8$, $R^9$ and $R^{10}$ independently of one another represent H, F, Cl, Br, I, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, $C_{3-8}$-cycloalkyl, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted, wherein $R^{13}$ represents H; $C_{1-5}$-alkyl, in each case saturated or unsaturated, branched or unbranched, unsubstituted or mono- or poly-substituted; $C_{3-8}$-cycloalkyl, in each case saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted;

$R^{14}$ and $R^{15}$ independently of one another represent H; $C_{1-5}$-alkyl, in each case saturated or unsaturated, branched or unbranched, unsubstituted or mono- or poly-substituted; or $C_{3-8}$-cycloalkyl, in each case saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted; or $R^{14}$ and $R^{15}$ together form $CH_2CH_2OCH_2CH_2$, $CH_2CH_2NR^{16}CH_2CH_2$ or $(CH_2)_{3-6}$, wherein $R^{16}$ represents H; $C_{1-5}$-alkyl, saturated or unsaturated, branched or unbranched, unsubstituted or mono- or poly-substituted;

X represents O, S, SO, $SO_2$ or $NR^{17}$, wherein $R^{17}$ represents H; $C_{1-5}$-alkyl, saturated or unsaturated, branched or unbranched; $COR^{12}$ or $SO_2R^{12}$;

in the form of the racemate; of the enantiomers, diastereoisomers, mixtures of the enantiomers or diastereoisomers or in the form of an individual enantiomer or diastereoisomer; in the form of the bases and/or salts of physiologically acceptable acids or cations.

When different radicals are combined, for example $R^7$, $R^8$, $R^9$ and $R^{10}$, and when radicals are combined with their substituents, such as, for example, $OR^{13}$, $SR^{13}$, $SO_2R^{13}$ or $COOR^{13}$, it is possible for a substituent, for example $R^{13}$, for two or more radicals, for example $R^7$, $R^8$, $R^9$ and $R^{10}$, to have different meanings within a substance.

The compounds according to the invention exhibit good binding to the µ receptor. Surprisingly, it has been shown that the substances also inhibit noradrenaline and serotonin reuptake.

As used herein, the expressions "$C_{1-5}$-alkyl" and "$C_{1-3}$-alkyl" include acyclic saturated or unsaturated hydrocarbon radicals, which can be straight- or branched-chained as well as unsubstituted or mono- or poly-substituted, having 1, 2, 3, 4 or 5 carbon atoms or 1, 2, or 3 carbon atoms, respectively, that is to say $C_{1-5}$-alkanyls, $C_{2-5}$-alkenyls and $C_{2-5}$-alkynyls or $C_{1-3}$-alkanyls, $C_{2-3}$-alkenyls and $C_{2-3}$-alkynyls. Alkenyls have at least one C—C double bond and alkynyls have at least one C—C triple bond. Alkyl is advantageously selected from the group comprising methyl, ethyl, n-propyl, 2-propyl, n-butyl, isobutyl, sec.-butyl, tert.-butyl, n-pentyl, isopentyl, neopentyl, n-hexyl, 2-hexyl; ethylenyl (vinyl), ethynyl, propenyl (—$CH_2CH=CH_2$, —CH=CH—$CH_3$, —C(=$CH_2$)—$CH_3$), propynyl (—CH—C≡CH, —C≡C—$CH_3$), 1,1-dimethylethyl, 1,1-dimethylpropyl, butenyl, butynyl, pentenyl and pentynyl.

The term "substituted" as used herein in association with "alkyl" is understood as meaning the replacement of one or more hydrogen atoms by F, Cl, Br, I, —CN, $NH_2$, NH-alkyl, NH-aryl, NH-heteroaryl, NH-cycloalkyl, NH-alkyl-aryl, NH-alkyl-heteroaryl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)$C_{1-6}$-alkyl, C(=S)$C_{1-6}$-alkyl, C(=O)aryl, C(=S)aryl, C(=O)$C_{1-6}$-alkyl-aryl, C(=O)$C_{1-6}$-alkyl-heteroaryl, C(=S)$C_{1-6}$-alkyl-aryl, C(=S)$C_{1-6}$-alkyl-heteroaryl, C(=O)-heteroaryl, C(=S)-heteroaryl, C(=O)-cycloalkyl, C(=S)-cycloalkyl, $CO_2H$, $CO_2$-alkyl, $CO_2$-alkyl-aryl, $CO_2$-alkyl-heteroaryl, C(=O)$NH_2$, C(=O)NH-alkyl, C(=O)NHaryl, C(=O)NH-heteroaryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, $SO_2$-alkyl, $SO_2NH_2$, $SO_3H$, PO(O—$C_{1-6}$-alkyl), cycloalkyl, aryl or heteroaryl, polysubstituted radicals being understood as meaning those radicals that are polysubstituted, for example di- or tri-substituted, either on different atoms or on the same atoms, for example trisubstituted on the same C atom as in the case of $CF_3$ or —$CH_2CF_3$ or at different positions as in the case of —CH(OH)—CH=CH—$CHCl_2$. Polysubstitution can be effected with the same or with different substituents. A substituent can optionally itself be substituted; accordingly, -Oalkyl also includes inter alia —O—$CH_2$—$CH_2$—O—$CH_2$—$CH_2$—OH.

For the purposes of this invention, the term "cycloalkyl" or "$C_{3-8}$-cycloalkyl" denotes cyclic hydrocarbons having 3, 4, 5, 6, 7 or 8 carbon atoms, wherein the hydrocarbons can be saturated or unsaturated (but not aromatic), unsubstituted or mono- or poly-substituted. In relation to cycloalkyl, the term also includes saturated or unsaturated (but not aromatic) cycloalkyl radicals in which one or two carbon atoms have been replaced by a heteroatom S, N or O. $C_{3-8}$-Cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

The term $(CH_2)_{3-6}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—.

Within the scope of this invention, the term "aryl" denotes carbocyclic ring systems having at least one aromatic ring but without heteroatoms in only one of the rings, including phenyls, naphthyls and phenanthrenyls, fluoranthenyls, fluorenyls, indanyls and tetralinyls. The aryl radicals can also be fused with further saturated, (partially) unsaturated or aromatic ring systems. Each aryl radical can be unsubstituted or mono- or poly-substituted, it being possible for the aryl substituents to be identical or different and to be located at any desired and possible position of the aryl. Phenyl or naphthyl radicals are particularly advantageous.

The term "heteroaryl" denotes a 5-, 6- or 7-membered cyclic aromatic radical which contains at least 1 heteroatom, optionally also 2, 3, 4 or 5 heteroatoms, the heteroatoms being identical or different and the heterocyclic radical being unsubstituted or mono- or poly-substituted; in the case of substitution on the heterocyclic radical, the substituents can be identical or different and can be located at any desired and possible position of the heteroaryl. The heterocyclic radical can also be part of a bi- or poly-cyclic system. Preferred heteroatoms are nitrogen, oxygen and sulfur. It is preferred for the heteroaryl radical to be selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, it being possible for the bond to the compounds of the general structure I to be effected via any desired and possible ring member of the heteroaryl radical.

Within the scope of this invention, "mono- or poly-substituted" in relation to "aryl", "heteroaryl" and "cycloalkyl" is understood as meaning the mono- or poly-substitution, for example di-, tri-, tetra- or penta-substitution, preferably mono- or di-substitution, of one or more hydrogen atoms of the ring system by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, $C(=O)C_{1-6}$-alkyl, $C(=S)C_{1-6}$-alkyl, $C(=O)$aryl, $C(=S)$aryl, $C(=O)C_{1-6}$-alkyl-aryl, $C(=O)C_{1-6}$-alkyl-heteroaryl, $C(=S)C_{1-6}$-alkyl-aryl, $C(=S)C_{1-6}$-alkyl-heteroaryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $CO_2$-alkyl-heteroaryl, $C(=O)NH_2$, $C(=O)NH$-alkyl, $C(=O)NH$aryl, $C(=O)NH$-cycloalkyl, $C(=O)N(alkyl)_2$, $C(=O)N(alkyl-aryl)_2$, $C(=O)N(alkyl-heteroaryl)_2$, $C(=O)N(cycloalkyl)_2$, S(O)-alkyl, S(O)-aryl, $SO_2$-alkyl, $SO_2$-aryl, $SO_2NH_2$, $SO_3H$, $CF_3$, =O, =S; alkyl, cycloalkyl, aryl and/or heteroaryl; on one atom or, optionally, on different atoms (it being possible for a substituent itself to be substituted). Polysubstitution is effected with the same or different substituents.

The term salt is to be understood as meaning any form of the active ingredient according to the invention in which the active ingredient assumes an ionic form or is charged and is coupled with a counterion (a cation or anion) or is in solution. The term is also to be understood as meaning complexes of the active ingredient with other molecules and ions, in particular complexes complexed via ionic interactions. In particular (and this is also a preferred embodiment of this invention), the term is understood as meaning physiologically acceptable salts, in particular physiologically acceptable salts with cations or bases and physiologically acceptable salts with anions or acids or alternatively a salt formed with a physiologically acceptable acid or with a physiologically acceptable cation.

Within the scope of this invention, the term of the physiologically acceptable salt with anions or acids is understood as meaning salts of at least one of the compounds according to the invention—in most cases protonated, preferably at the nitrogen—as cation with at least one anion, which are physiologically acceptable—in particular when used in humans and/or mammals. Within the scope of this invention, the term is understood as meaning in particular the salt formed with a physiologically acceptable acid, namely salts of the active ingredient in question with inorganic or organic acids, which are physiologically acceptable—in particular when used in humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharinic acid, monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, phosphoric acid, maleic acid, malonic acid, hippuric acid and/or aspartic acid. Particular preference is given to the hydrochloride salt, the citrate and the sesquicitrate.

Within the scope of this invention, the term "physiologically acceptable salt with cations or bases" is understood as meaning salts of at least one of the compounds according to the invention—in most cases of a (deprotonated) acid—as anion with at least one cation, preferably an inorganic cation, which are physiologically acceptable—in particular when used in humans and/or mammals. Particular preference is given to the salts of the alkali and alkaline earth metals but also to ammonium salts, but in particular to (mono-) or (di-) sodium, (mono-) or (di-)potassium, magnesium or calcium salts.

In one preferred embodiment of the spirocyclic cyclohexane compounds according to the invention, $R^1$ and $R^2$ independently of one another represent H; $C_{1-5}$-alkyl, saturated or unsaturated, branched or unbranched, mono- or poly-substituted or unsubstituted, or $R^1$ and $R^2$ together form a ring and represent $CH_2CH_2OCH_2CH_2$, $CH_2CH_2NR^{11}CH_2CH_2$ or $(CH_2)_{3-6}$, wherein $R^{11}$ represents H; $C_{1-5}$-alkyl, saturated or unsaturated, branched or unbranched, mono- or poly-substituted or unsubstituted.

Particular preference is given to spirocyclic cyclohexane compounds wherein $R^1$ and $R^2$ independently of one another represent $CH_3$ or H, wherein $R^1$ and $R^2$ do not simultaneously represent H.

Also preferred are spirocyclic cyclohexane compounds wherein $R^3$ represents phenyl, unsubstituted or mono- or poly-substituted, preferably mono- or poly-substituted by F, Cl, CN, $OCH_3$, $SCH_3$, $OCH_2CH_3$, $CH_3$, $CF_3$ or by OH, in particular phenyl, 3-methoxyphenyl, 2-methylphenyl, 4-trifluoromethylphenyl, 4-methylthiophenyl, 3-fluorophenyl and 4-fluorophenyl.

Preference is given further to spirocyclic cyclohexane compounds wherein W represents $NR^4$, O or S and X represents $NR^{17}$, O or S.

Particular preference is given to spirocyclic cyclohexane compounds wherein W represents NH, O or S and X represents NH, $NC(O)CH_3$, O or S.

In addition, preference is also given to spirocyclic cyclohexane compounds wherein $R^7$, $R^8$, $R^9$ and $R^{10}$ independently of one another represent H; $C_{1-5}$-alkyl, branched or unbranched, unsubstituted or mono- or poly-substituted; F, Cl, Br, I, $CF_3$, OH, $OCH_3$, $NH_2$, COOH, $COOCH_3$, $NHCH_3$ or $N(CH_3)_2$ or $NO_2$, in particular H, F or $OCH_3$.

Preference is additionally given to spirocyclic cyclohexane compounds wherein $R^5$ represents H, $C_{1-5}$-alkyl, branched or unbranched, unsubstituted or mono- or poly-substituted, or $COOR^{13}$ and $R^6$ represents H or $C_{1-5}$-alkyl, in particular $R^5$ and $R^6$ represent H.

Particular preference is given to spirocyclic cyclohexane compounds wherein the radicals $R^5$ to $R^{10}$ represent H.

Very particular preference is given to spirocyclic cyclohexane compounds selected from the group consisting of:

1,1-(2-(dimethylaminomethyl)-3-hydroxy-3-(3-methoxyphenyl)-pentamethylene)-3,4-dihydro-1H-2,9-diazafluorene dihydrochloride 1,1-(2-(dimethylaminomethyl)-3-hydroxy-3-(3-methoxyphenyl)-pentamethylene)-2-acetyl-3,4-dihydro-1H-2,9-diazafluorene hydrochloride 1,1-(2-(dimethylaminomethyl)-3-hydroxy-3-(3-fluorophenyl)-pentamethylene)-3,4-dihydro-1H-2,9-diazafluorene citrate 1,1-(2-(dimethylaminomethyl)-3-hydroxy-3-phenyl-pentamethylene)-1,3,4,9-tetrahydro-pyrano[3,4-b]indole sesquicitrate 1,1-(2-(dimethylaminomethyl)-3-hydroxy-3-phenyl-pentamethylene)-1,3,4,9-tetrahydro-pyrano[3,4-b]benzofuran citrate 1,1-(2-(dimethylaminomethyl)-3-hydroxy-3-(2-methylphenyl)-pentamethylene)-3,4-dihydro-1H-2,9-diazafluorene citrate 1,1-(2-(dimethylaminomethyl)-3-hydroxy-3-phenyl-pentamethylene)-1,3,4,9-tetrahydro-pyrano[3,4-b]benzothiophene citrate 1,1-(2-(dimethylaminomethyl)-3-hydroxy-3-(3-fluorophenyl)-pentamethylene)-1,3,4,9-tetrahydro-pyrano[3,4-b]benzofuran citrate 1,1-(2-(dimethylaminomethyl)-3-hydroxy-3-phenyl-pentamethylene)-1,3,4,9-tetrahydro-2-thia-9-aza-fluorene citrate 1,1-(2-(dimethylaminomethyl)-3-hydroxy-3-(3-fluorophenyl)-pentamethylene)-1,3,4,9-tetrahydro-pyrano[3,4-b]benzothiophene citrate 1,1-(2-(dimethylaminomethyl)-3-hydroxy-3-(2-methylphenyl)-pentamethylene)-1,3,4,9-tetrahydro-pyrano[3,4-b]benzothiophene citrate 1,1-(2-(dimethylaminomethyl)-3-hydroxy-3-(2-methylphenyl)-pentamethylene)-1,3,4,9-tetrahydro-pyrano[3,4-b]benzofuran citrate 1,1-(2-(dimethylaminomethyl)-3-hydroxy-3-(4-trifluoromethylphenyl)-pentamethylene)-1,3,4,9-tetrahydro-pyrano[3,4-b]benzofuran citrate 1,1-(2-(dimethylaminomethyl)-3-hydroxy-3-(3-fluorophenyl)-pentamethylene)-1,3,4,9-tetrahydro-2-thia-9-aza-fluorene citrate 1,1-(2-(dimethylaminomethyl)-3-hydroxy-3-(4-trifluoromethylphenyl)-pentamethylene)-3,4-dihydro-1H-2,9-diazafluorene dicitrate 1,1-(2-(dimethylaminomethyl)-3-hydroxy-3-(3-fluorophenyl)-pentamethylene)-7-fluoro-3,4-dihydro-1H-2,9-diazafluorene sesquicitrate 1,1-(2-(dimethylaminomethyl)-3-hydroxy-3-phenyl-pentamethylene)-3,4-dihydro-6-methoxy-1H-2,9-diazafluorene citrate 1,1-(2-(dimethylaminomethyl)-3-hydroxy-3-(4-methylthiophenyl)-pentamethylene)-1,3,4,9-tetrahydro-6-methoxy-pyrano[3,4-b]indole citrate 1,1-(2-(dimethylaminomethyl)-3-hydroxy-3-(2-methylphenyl)-pentamethylene)-1,3,4,9-tetrahydro-6-methoxy-pyrano[3,4-b]indole citrate 1,1-(2-(dimethylaminomethyl)-3-hydroxy-3-(4-methylthiophenyl)-pentamethylene)-1,3,4,9-tetrahydro-pyrano[3,4-b]indole citrate 1,1-(2-(dimethylaminomethyl)-3-hydroxy-3-(3-fluorophenyl)-pentamethylene)-3,4-dihydro-6-methoxy-1H-2,9-diazafluorene citrate 1,1-(2-(dimethylaminomethyl)-3-hydroxy-3-(4-trifluoromethylphenyl)-pentamethylene)-3,4-dihydro-6-methoxy-1H-2,9-diazafluorene citrate 1,1-(2-(dimethylaminomethyl)-3-hydroxy-3-(4-methylthiophenyl)-pentamethylene)-1,3,4,9-tetrahydro-2-thia-9-aza-fluorene sesquicitrate 1,1-(2-(dimethylaminomethyl)-3-hydroxy-3-(2-methylphenyl)-pentamethylene)-1,3,4,9-tetrahydro-2-thia-9-aza-fluorene citrate 1,1-(2-(dimethylaminomethyl)-3-hydroxy-3-(2-methylphenyl)-pentamethylene)-1,3,4,9-tetrahydro-pyrano[3,4-b]indole citrate 1,1-(2-(dimethylaminomethyl)-3-hydroxy-3-(4-methylthiophenyl)-pentamethylene)-3,4-dihydro-1H-2,9-diazafluorene citrate 1,1-(2-(dimethylaminomethyl)-3-hydroxy-3-(3-fluorophenyl)-pentamethylene)-1,3,4,9-tetrahydro-pyrano[3,4-b]indole hydrochloride 1,1-(2-(dimethylaminomethyl)-3-hydroxy-3-phenyl-pentamethylene)-3,4-dihydro-1H-2,9-diazafluorene citrate 1,1-(2-(dimethylaminomethyl)-3-hydroxy-3-(4-trifluoromethylphenyl)-pentamethylene)-1,3,4,9-tetrahydro-pyrano[3,4-b]benzothiophene citrate 1,1-(2-(dimethylaminomethyl)-3-hydroxy-3-(4-methylthiophenyl)-pentamethylene)-1,3,4,9-tetrahydro-pyrano[3,4-b]benzofuran citrate 1,1-(2-(dimethylaminomethyl)-3-hydroxy-3-(4-methylthiophenyl)-pentamethylene)-1,3,4,9-tetrahydro-pyrano[3,4-b]benzothiophene citrate 1,1-(2-(dimethylaminomethyl)-3-hydroxy-3-(2-methylphenyl)-pentamethylene)-7-fluoro-3,4-dihydro-1H-2,9-diazafluorene citrate 1,1-(2-(dimethylaminomethyl)-3-hydroxy-3-(4-trifluoromethylphenyl)-pentamethylene)-7-fluoro-3,4-dihydro-1H-2,9-diazafluorene citrate 1,1-(2-(dimethylaminomethyl)-3-hydroxy-3-(4-methylthiophenyl)-pentamethylene)-7-fluoro-3,4-dihydro-1H-2,9-diazafluorene citrate 1,1-(2-(dimethylaminomethyl)-3-hydroxy-3-phenyl-pentamethylene)-7-fluoro-3,4-dihydro-1H-2,9-diazafluorene dicitrate in the form of the racemate; of the enantiomers, diastereoisomers, mixtures of the enantiomers or diastereoisomers or in the form of an individual enantiomer or diastereoisomer; in the form of the bases and/or salts of physiologically acceptable acids or cations.

The substances according to the invention act, for example, on the μ-opioid receptor, which is relevant in connection with various diseases, so that they are suitable as a pharmaceutical active ingredient in a medicament. The invention therefore further provides medicaments comprising at least one spirocyclic cyclohexane derivative according to the invention as well as, optionally, suitable additives and/or auxiliary substances and/or optionally further active ingredients.

In addition to at least one spirocyclic cyclohexane derivative according to the invention, the medicaments according to the invention optionally comprise suitable additives and/or auxiliary substances, that is to say also carrier materials, fillers, solvents, diluents, colorings and/or binders, and can be administered as liquid medicament forms in the form of injection solutions, drops or juices, as semi-solid medicament forms in the form of granules, tablets, pellets, patches, capsules, plasters/spray-on plasters or aerosols. The choice of the auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example to the skin, the mucous membranes or in the eyes. Preparations in the form of tablets, dragées, capsules, granules, drops, juices and syrups are suitable for oral administration, and solutions, suspensions, readily reconstitutable dry formulations and sprays are suitable for parenteral, topical and inhalatory administration. Spirocyclic cyclohexane compounds according to the invention in a depot, in dissolved form or in a plaster, optionally with the addition of agents that promote penetration through the skin, are suitable formulations for percutaneous administration. Forms of preparation which can be used orally or percutaneously can release the spirocyclic cyclohexane compounds according to the invention in a delayed manner. The spirocyclic cyclohexane compounds according to the invention can also be administered in parenteral long-term depot forms, such as, for example, implants or implanted pumps. Other further active ingredients known to the person skilled in the art can in principle be added to the medicaments according to the invention.

The amount of active ingredient to be administered to the patients varies according to the weight of the patient, the mode of administration, the indication and the severity of the disease. From 0.00005 to 50 mg/kg, preferably from 0.01 to 5 mg/kg, of at least one spirocyclic cyclohexane derivative according to the invention are conventionally administered.

For all the above forms of the medicaments according to the invention, it is preferable if, in addition to at least one spirocyclic cyclohexane derivative, the medicament also comprises a further active ingredient, in particular an opioid, preferably a potent opioid, in particular morphine, or an anaesthetic, preferably hexobarbital or halothane.

In a preferred form of the medicament, a spirocyclic cyclohexane derivative according to the invention contained therein is present in the form of a non-equimolar or equimolar mixture of the diastereoisomers and/or enantiomers, particularly preferably in the form of a pure diastereoisomer and/or enantiomer.

The μ-opioid receptor, as well as the other opioid receptors, have been identified particularly in the occurrence of pain. Accordingly, spirocyclic cyclohexane compounds according to the invention can be used in the preparation of a medicament and for the treatment of pain, in particular of acute, visceral, neuropathic or chronic pain.

The invention therefore relates further to the use of a spirocyclic cyclohexane derivative according to the invention in the preparation of a medicament and for the treatment of pain, in particular of acute, visceral, neuropathic or chronic pain.

Surprisingly, it has been shown that the spirocyclic cyclohexane compounds according to the invention are suitable for the treatment of anxiety, depression, epilepsy, cardiovascular diseases, urinary incontinence, diarrhea, pruritus, alcohol and drug abuse, medicament dependency, inflammations, lack of drive, bulimia, anorexia, catalepsy, for use as a local anaesthetic, anti-arrhythmic, anti-emetic, nootropic agent, and for increasing vigilance and libido. The invention therefore further relates to the use of a spirocyclic cyclohexane derivative according to the invention in the preparation of a medicament for the treatment of anxiety, depression, epilepsy, cardiovascular diseases, urinary incontinence, diarrhea, pruritus, alcohol and drug abuse, medicament dependency, inflammations, lack of drive, bulimia, anorexia, catalepsy, for use as a local anaesthetic, anti-arrhythmic, anti-emetic, nootropic agent, and for increasing vigilance and libido.

It can be preferable in one of the above uses if a spirocyclic cyclohexane derivative that is used is in the form of a non-equimolar or equimolar mixture of the diastereoisomers and/or enantiomers, in particular in the form of a pure diastereoisomer and/or enantiomer.

The invention further provides a method of treating, in particular in one of the above-mentioned indications, a non-human mammal or a human requiring treatment of pain, in particular of chronic pain, by administration of a therapeutically effective dose of a spirocyclic cyclohexane derivative according to the invention or of a medicament according to the invention.

The invention further provides a process for the preparation of the spirocyclic cyclohexane compounds according to the invention as described in the following description and examples.

$R^{01}$ and $R^{02}$ are as defined for $R^1$ and $R^2$ for the compounds of formula I according to the invention and can additionally, independently of one another, represent a protecting group:

General synthesis scheme I:

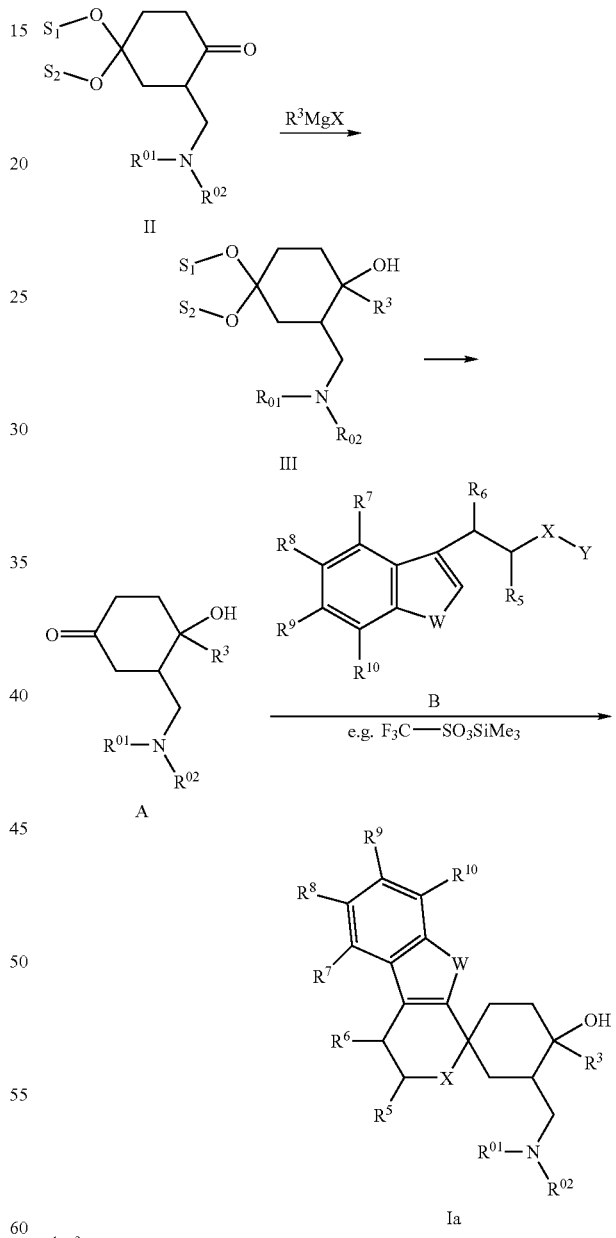

$S^1$, $S^2$ protecting groups
X = O, S
Y = H, Si(CH$_3$)$_3$

The synthesis of 7-dialkylaminomethyl-1,4-dioxa-spiro[4.5]decan-8-one is described in EP0780369 for $R^1$, $R^2$=methyl.

A Mannich base of formula II, wherein S1 and S2 represent protecting groups, preferably a ketal protecting group, is reacted at a temperature of from −40° C. to +60° C., in diethyl ether, tetrahydrofuran or dioxane, with an organometallic compound, preferably with an aromatic Grignard compound of formula $R^3MgX$ (X=I, Br, Cl) or with an organolithium compound of formula $R^3Li$, to give a compound of formula III.

In the compound of formula III, the protecting groups are removed with acid, preferably with aqueous acid, particularly preferably with hydrochloric acid, optionally in the presence of an organic solvent such as, for example, tetrahydrofuran or diethyl ether, at a temperature of from −20° C. to +40° C., preferably from 0° C. to room temperature, and the ketone A is obtained.

The resulting ketone A is reacted with a tryptophol, benzofuran-3-ylethanol or benzothiophen-3-ylethanol derivative, preferably with the corresponding silyl ethers, particularly preferably with the corresponding trimethylsilyl ethers, in the presence of suitable coupling reagents, to give the products Ia (X=O). Suitable coupling reagents are strong acids such as, for example, trifluoroacetic acid, methanesulfonic acid or a mixture of phosphoric acid and glacial acetic acid; or silyl esters of said acids, such as, for example, trifluoromethanesulfonic acid trimethylsilyl ester. The couplings are carried out at temperatures of from −10° C. to +40° C., preferably from 0° C. to room temperature, in an organic solvent, preferably di- or tri-chloromethane or dichloroethane, or the acid itself is used as solvent. The corresponding indol-3-ylethanethiol, benzofuran-3-ylethanethiol or benzothiophen-3-ylethanethiol derivatives are reacted analogously to give the end products Ia (X=S).

General synthesis route II (β-carbolines):

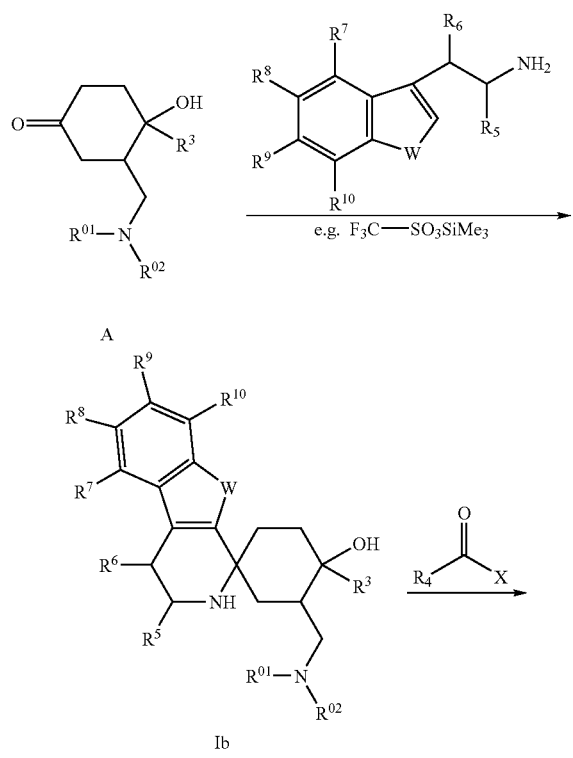

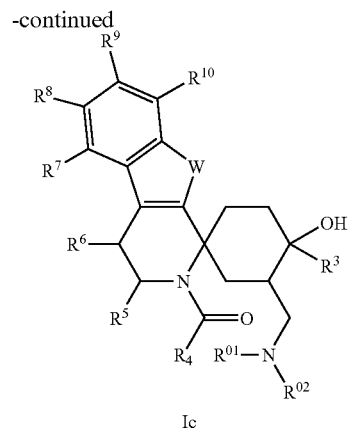

The ketone A (see General synthesis scheme I) is reacted with a tryptamine, benzofuran-3-ylethylamine or benzothiophen-3-ylethylamine derivative in the presence of suitable coupling reagents to give the products Ib. Suitable coupling reagents are strong acids such as, for example, trifluoroacetic acid, methanesulfonic acid or a mixture of phosphoric acid and glacial acetic acid; or silyl esters of said acids, such as, for example, trifluoromethanesulfonic acid trimethylsilyl ester. The couplings are carried out at temperatures of from −10° C. to +40° C., preferably from 0° C. to room temperature, in an organic solvent, preferably in an alcohol, particularly preferably in methanol, and then in di- or tri-chloromethane or 1,2-dichloroethane.

The products Ib can be reacted in a subsequent step with acid halides or anhydrides in the presence of a base, for example triethylamine, pyridine or (dimethylamino)pyridine, to give the corresponding amides Ic. This reaction preferably takes place with microwave irradiation.

Spirocyclic cyclohexane compounds of formula I wherein X represents SO or $SO_2$ can be obtained by reacting spirocyclic cyclohexane compounds of formula I wherein X represents S with an oxidising agent, for example $H_2O_2$.

EXAMPLES

The following Examples serve to explain the invention in greater detail but do not limit the general inventive idea. The yields of the prepared compounds are not optimized. All temperatures are uncorrected.

The term "ether" denotes diethyl ether, "EE" denotes ethyl acetate and "DCM" denotes dichloromethane. The term "equivalents" means substance equivalents, "m.p." means melting point or melting range, "decomp." means decomposition, "RT" means room temperature, "abs." means absolute (anhydrous), "rac." means racemic, "conc." means concentrated, "min." means minutes, "h" means hours, "d" means days, "vol. %" means percent by volume, "m %" means percent by weight and "M" is the concentration in mol/l.

Silica gel 60 (0.040-0.063 mm) from E. Merck, Darmstadt was used as the stationary phase for column chromatography. Thin-layer chromatographic analyses were carried out using HPTLC pre-coated plates, silica gel 60 F 254, from E. Merck, Darmstadt. The mixing ratios of mobile phases for chromatographic analyses are always given in volume/volume.

The compounds used hereinbelow were either commercially available, or their preparation is known from the prior art or has been derived from the prior art in a manner obvious to the person skilled in the art.

3-Dimethylaminomethyl-4-phenyl-4-hydroxy-cyclohexanone hydrochloride 215 ml of hydrochloric acid (32%, excess) were added rapidly at 0° C. to a solution of 7-dimethylaminomethyl-8-phenyl-1,4-dioxa-spiro[4.5]decan-8-ol hydrochloride (85 g, 259 mmol) in tetrahydrofuran/water mixture, and stirring was then carried out for 16 hours at RT. The resulting colorless solid was filtered out with suction and dried. 47.5 g (65%) of the product were obtained.

3-Dimethylaminomethyl-4-(3-fluorophenyl)-4-hydroxy-cyclohexanone methanesulfonate 11.4 ml of hydrochloric acid (32%, excess) were added rapidly at 0° C. to a solution of 7-dimethylaminomethyl-8-(3-fluorophenyl)-1,4-dioxa-spiro[4.5]decan-8-ol hydrochloride (10.83 g, 31.3 mmol) in tetrahydrofuran/water mixture, and stirring was then carried out for 16 hours at RT. The mixture was adjusted to pH 11 with 32% sodium hydroxide solution, and extraction was carried out with ether. After evaporation of the solvent in vacuo, the residue was taken up in diisopropyl ether and EE, and the corresponding salt was precipitated by addition of methanesulfonic acid (1.88 ml, 28.9 mmol). 4.92 g (53%) of the product were obtained in the form of a colorless solid.

3-Dimethylaminomethyl-4-(2-methylphenyl)-4-hydroxy-cyclohexanone methanesulfonate 178 ml of hydrochloric acid (32%, excess) were added rapidly at 0° C. to a solution of 7-dimethylaminomethyl-8-(2-methyl-phenyl)-1,4-dioxa-spiro[4.5]decan-8-ol hydrochloride (73.5 g, 215 mmol) in tetrahydrofuran/water mixture, and stirring was then carried out for 16 hours at RT. The mixture was adjusted to pH 12 with 32% sodium hydroxide solution, and extraction was carried out with ether. After evaporation of the solvent in vacuo, the residue was taken up in diisopropyl ether and EE, and the corresponding salt was precipitated by addition of methanesulfonic acid (13 ml, 200 mmol). 64.3 g (84%) of the product were obtained in the form of a colorless solid.

3-Dimethylaminomethyl-4-(4-trifluoromethyl-phenyl)-4-hydroxy-cyclohexanone hydrochloride 60 ml of hydrochloric acid (32%, excess) were added rapidly at 0° C. to a solution of 7-dimethylaminomethyl-8-(3-fluoro-phenyl)-1,4-dioxa-spiro[4.5]decan-8-ol hydrochloride (35.9 g, 90.7 mmol) in tetrahydrofuran/water mixture, and stirring was then carried out for 16 hours at RT. The mixture was adjusted to pH 11 with 32% sodium hydroxide solution, and extraction was carried out with ether. After evaporation of the solvent in vacuo, the residue was taken up in 200 ml of ethyl methyl ketone, and the hydrochloride was precipitated by addition of trimethylchlorosilane (11.2 ml) and water (0.8 ml). 23.5 g (74%) of the product were obtained in the form of a colorless solid.

3-Dimethylaminomethyl-4-(4-methylthio-phenyl)-4-hydroxy-cyclohexanone hydrochloride 70 ml of hydrochloric acid (32%, excess) were added rapidly at 0° C. to a solution of 7-dimethylaminomethyl-8-(3-fluoro-phenyl)-1,4-dioxa-spiro[4.5]decan-8-ol hydrochloride (41.0 g, 104 mmol) in tetrahydrofuran/water mixture, and stirring was then carried out for 16 hours at RT. The resulting colorless solid was filtered off with suction and dried. 20.8 g (57%) of the product were obtained.

2-Benzo[b]thiophen-3-yl-ethanol

A solution of benzo[b]thiophen-3-yl-acetic acid (6.0 g, 31.2 mmol) in 40 ml of tetrahydrofuran was added dropwise at RT to a suspension of lithium alanate (1.54 g, 41 mmol) in 35 ml of tetrahydrofuran. The mixture was stirred for 60 minutes at 60° C., and then excess alanate was hydrolysed with ethanol. The mixture was suction-filtered over Kieselguhr and the solvent was removed in vacuo. The product was obtained in the form of a yellowish oil in a yield of 5.1 g (92%).

2-Benzofuran-3-yl-ethanol

A solution of benzofuran-3-yl-acetic acid methyl ester (4.0 g, 21 mmol) in 25 ml of ether was added dropwise at RT to a suspension of lithium alanate (1.61 g, 59.5 mmol) in 35 ml of ether, and stirring was then carried out for 30 minutes. Excess alanate was then hydrolysed with ethanol, the mixture was suction-filtered over Kieselguhr, and the solvent was removed in vacuo. The product was obtained in the form of a yellowish oil in a yield of 3.0 g (89%).

Thiosulfuric acid S-[2-(1H-indol-3-yl)-ethyl]ester, O-sodium salt

A solution of 3-(2-bromo-ethyl)-1H-indole (5.0 g, 22.3 mmol) in 63 ml of ethanol was added dropwise at RT to a solution of sodium thiosulfate (6.0 g, 37.9 mmol) in 38 ml of water. The mixture was refluxed for 30 minutes, and then the solvent was removed by distillation in vacuo. The residue was suspended in 110 ml of isopropanol and refluxed. The undissolved residue was filtered out with suction at elevated temperature and, upon cooling, the product precipitated from the filtrate in the form of a colorless precipitate (5.1 g, 82%).

2-(1H-Indol-3-yl)-ethanethiol

Thiosulfuric acid S-[2-(1H-indol-3-yl)-ethyl]ester, O-sodium salt (5.04 g, 18 mmol) was suspended in 105 ml of 50% phosphoric acid and covered with a layer of 160 ml of ether. The mixture was refluxed for 6 hours. After cooling, the phases were separated and the aqueous phase was extracted with ether and the organic phases were concentrated to dryness by evaporation. The crude product was obtained in a yield of 3.2 g (100%).

1,1-(2-Dimethylaminomethyl)-3-hydroxy-3-(3-methoxyphenyl)-pentamethylene)-3,4-dihydro-1H-2,9-diazafluorene 3-Dimethylaminomethyl-4-hydroxy-4-(3-methoxy-phenyl)-cyclohexanone (1.387 g, 5 mmol) and tryptamine (800 mg, 5 mmol) were dissolved in 50 ml of dry 1,2-dichloroethane. Trifluoroacetic acid (770 µl, 10 mmol) and sodium sulfate (2 g) were added, with stirring. After 15 hours, a further 3 ml of trifluoroacetic acid were added to the reaction mixture, and stirring was continued for a further 12 hours at RT. After concentration in vacuo, water (20 ml) was added to the residue, the pH was adjusted to 11 with 5M NaOH, and extraction was carried out with EE. After concentration, the residue was purified by chromatography on silica gel with EE/ethanol (1:1) and the product was obtained in a yield of 600 mg (29%) in the form of a colorless solid.

1,1-(2-Dimethylaminomethyl)-3-hydroxy-3-(3-methoxyphenyl)-pentamethylene)-3,4-dihydro-1H-2,9-diazafluorene dihydrochloride

Example 1

In order to prepare the hydrochloride, 1,1-(2-dimethylaminomethyl)-3-hydroxy-3-(3-methoxyphenyl)pentamethylene)-3,4-dihydro-1H-2,9-diazafluorene (300 mg, 0.72 mmol) was dissolved in ethyl methyl ketone (5 ml), and chlorotrimethylsilane (237 μl, 1.79 mmol) was added thereto. The resulting solid was filtered off with suction and dried. The hydrochloride was obtained in a yield of 350 mg (100%) in the form of a colorless solid (m.p. 236-238° C.).

1,1-(2-Dimethylaminomethyl)-3-hydroxy-3-(3-methoxyphenyl)-pentamethylene)-2-acetyl-3,4-dihydro-1H-2,9-diazafluorene 1,1-(2-Dimethylaminomethyl)-3-hydroxy-3-(3-methoxyphenyl)-pentamethylene)-3,4-dihydro-1H-2,9-diazafluorene (300 mg, 0.72 mmol) was dissolved in pyridine (5 ml). Acetic anhydride (674 μl, 7.2 mmol) was added dropwise, and stirring was carried out for 48 hours at RT. The pyridine was distilled off in vacuo, the residue was taken up in 10 ml of water, the pH was adjusted to 11 with 5M NaOH, and extraction was carried out with EE. After concentration, the product was obtained in a yield of 323 mg (98%) in the form of a colorless solid.

1,1-(2-Dimethylaminomethyl)-3-hydroxy-3-(3-methoxyphenyl)-pentamethylene)-2-acetyl-3,4-dihydro-1H-2,9-diazafluorene hydrochloride

Example 2

In order to prepare the hydrochloride, 1,1-(2-dimethylaminomethyl)-3-hydroxy-3-(3-methoxyphenyl)pentamethylene)-2-acetyl-3,4-dihydro-1H-2,9-diazafluorene (323 mg, 0.7 mmol) was dissolved in 5 ml of ethyl methyl ketone, and chlorotrimethylsilane (139 μl, 1.05 mmol) was added thereto. The solid that precipitated thereby was filtered off with suction. The hydrochloride was obtained in a yield of 348 mg (100%) in the form of a colorless solid (m.p. 175-177° C.).

1,1-(2-(Dimethylaminomethyl)-3-hydroxy-3-(3-fluorophenyl)-pentamethylene)-3,4-dihydro-1H-2,9-diazafluorene 3-Dimethylaminomethyl-4-(3-fluorophenyl)-4-hydroxy-cyclohexanone (1.2 g, 4.5 mmol) and tryptamine (0.72 g, 4.5 mmol) were dissolved in dry methanol, and sodium sulfate (1.7 g) was added thereto. After 24 hours, the solvent was removed by distillation and the residue was suspended in 36 ml of 1,2-dichloroethane. Trifluoroacetic acid (3.5 ml) was added dropwise at 0° C., and stirring was then carried out for 24 hours at RT. Water was then added at 0° C. and the pH was adjusted to 11 with 5M sodium hydroxide solution. The phases were separated and the aqueous phase was extracted with 1,2-dichloroethane. After concentration, the crude product was chromatographed on silica gel (eluant: ether+0.3% ammonia). 329 mg (0.8 mmol, 18%) of the desired product were obtained.

1,1-(2-(Dimethylaminomethyl)-3-hydroxy-3-(3-fluorophenyl)-pentamethylene)-3,4-dihydro-1H-2,9-diazafluorene citrate

Example 3

1,1-(2-(Dimethylaminomethyl)-3-hydroxy-3-(3-fluorophenyl)-pentamethylene)-3,4-dihydro-1H-2,9-diazafluorene (329 mg, 0.8 mmol) was dissolved in 2 ml of ethanol, and citric acid (155 mg, 0.8 mmol) was added thereto. The citrate was obtained in the form of a colorless solid (374 mg, 78%).

1,1-(2-(Dimethylaminomethyl)-3-hydroxy-3-phenyl-pentamethylene)-1,3,4,9-tetrahydro-pyrano[3,4-b]indole 3-Dimethylaminomethyl-4-phenyl-4-hydroxy-cyclohexanone (1 g, 4.0 mmol) and tryptophol (0.65 g, 4.0 mmol) were dissolved in 40 ml of dichloromethane. Trifluoromethanesulfonic acid trimethylsilyl ester was added dropwise at 0° C., and stirring was then carried out for 24 hours at RT. The mixture was hydrolysed with water at 0° C. and adjusted to pH 11 with 1M sodium hydroxide solution. The phases were separated and the aqueous phase was extracted with dichloromethane. After concentration and drying, 1.48 g (3.8 mmol, 95%) of the crude product were obtained.

1,1-(2-(Dimethylaminomethyl)-3-hydroxy-3-phenyl-pentamethylene)-1,3,4,9-tetrahydro-pyrano[3,4-b]indole sesquicitrate

Example 4

1,1-(2-(Dimethylaminomethyl)-3-hydroxy-3-phenyl-pentamethylene)-1,3,4,9-tetrahydro-pyrano[3,4-b]indole (1.48 g, 3.8 mmol) was dissolved in 4 ml of ethanol, and citric acid (730 mg, 3.8 mmol) was added thereto. 2.13 g (3.14 mmol, 83%) of the product were obtained.

1,1-(2-(Dimethylaminomethyl)-3-hydroxy-3-phenyl-pentamethylene)-1,3,4,9-tetrahydro-pyrano[3,4-b]benzofuran citrate 3-Dimethylaminomethyl-4-phenyl-4-hydroxy-cyclohexanone (989 mg, 4.0 mmol) and 2-benzofuran-3-yl-ethanol (649 mg, 4.0 mmol) were dissolved in 20 ml of dichloromethane. At RT, trifluoromethanesulfonic acid trimethylsilyl ester (0.8 ml, 4.14 mmol) was added dropwise and stirring was carried out for 2 hours. After 30 minutes' stirring with 20 ml of 1M sodium hydroxide solution, the phases were separated and the aqueous phase was extracted with dichloromethane. After concentration, the crude product was chromatographed on silica gel (eluant: dichloromethane/methanol 19:1). The product was obtained in the form of a yellow foam (1.1 g, 73%).

1,1-(2-(Dimethylaminomethyl)-3-hydroxy-3-phenyl-pentamethylene)-1,3,4,9-tetrahydro-pyrano[3,4-b]benzofuran citrate

Example 5

1,1-(2-(Dimethylaminomethyl)-3-hydroxy-3-phenyl-pentamethylene)-1,3,4,9-tetrahydro-pyrano[3,4-b]benzofuran (1.1 g, 2.9 mmol) was dissolved in 10 ml of ethanol, and citric acid (560 mg, 2.9 mmol) was added thereto. After concentration, the product was obtained in the form of a light-yellow foam (1.6 g, 95%).

1,1-(2-(Dimethylaminomethyl)-3-hydroxy-3-(2-methylphenyl)-pentamethylene)-3,4-dihydro-1H-2,9-diazafluorene 3-Dimethylaminomethyl-4-(2-methylphenyl)-4-hydroxy-cyclohexanone (1.0 g, 3.8 mmol) and tryptamine (0.61 g, 3.8 mmol) were dissolved in 30 ml of dry methanol. After addition of sodium sulfate (1.5 g), stirring was carried out for 24 hours at room temperature. The solvent was removed by distillation, the residue was suspended in 30 ml of 1,2-dichloroethane, and 3 ml of trifluoroacetic acid were added thereto. After 24 hours' stirring at RT, 25 ml of water were added to the mixture at 0° C. and the pH was adjusted to 11 with 5M sodium hydroxide solution. Stirring was carried out for 30 minutes, the phases were separated, and extraction was carried out with 1,2-dichloroethane. The solution was concentrated and taken up in ether. The crude product was obtained in the form of a colorless solid (338 mg, 22%).

1,1-(2-(Dimethylaminomethyl)-3-hydroxy-3-(2-methylphenyl)-pentamethylene)-3,4-dihydro-1H-2,9-diazafluorene citrate

Example 6

1,1-(2-(Dimethylaminomethyl)-3-hydroxy-3-(2-methylphenyl)-pentamethylene)-3,4-dihydro-1H-2,9-diazafluorene (338 mg, 0.84 mmol) was dissolved in 8 ml of ethanol, and citric acid (161 mg, 0.84 mmol) was added thereto. The product was obtained in the form of a colorless precipitate (290 mg, 58%).

1,1-(2-(Dimethylaminomethyl)-3-hydroxy-3-phenyl-pentamethylene)-1,3,4,9-tetrahydro-pyrano[3,4-b]benzothiophene 3-Dimethylaminomethyl-4-phenyl-4-hydroxy-cyclohexanone (989 mg, 4.0 mmol) and 2-benzo[b]thiophen-3-yl-ethanol (713 mg, 4.0 mmol) were dissolved in 20 ml of dichloromethane. At RT, trifluoromethanesulfonic acid trimethylsilyl ester (0.8 ml, 4.14 mmol) was added dropwise and the mixture was then stirred for 2 hours. Stirring was then carried out for 30 minutes with 20 ml of 1M sodium hydroxide solution. The phases were separated and the aqueous phase was extracted with dichloromethane. A colorless foam was obtained as the crude product (1.53 g, 94%).

1,1-(2-(Dimethylaminomethyl)-3-hydroxy-3-phenyl-pentamethylene)-1,3,4,9-tetrahydro-pyrano[3,4-b]benzothiophene citrate

Example 7

1,1-(2-(Dimethylaminomethyl)-3-hydroxy-3-phenyl-pentamethylene)-1,3,4,9-tetrahydro-pyrano[3,4-b]benzothiophene (1.53 g, 3.8 mmol) was dissolved in 10 ml of ethanol, and 748 mg of citric acid were added thereto. After 16 hours, the mixture was concentrated and an almost colorless foam was isolated as the product (2.0 g, 88%).

1,1-(2-(Dimethylaminomethyl)-3-hydroxy-3-(3-fluorophenyl)-pentamethylene)-1,3,4,9-tetrahydro-pyrano[3,4-b]benzofuran 3-Dimethylaminomethyl-4-(3-fluorophenyl)-4-hydroxy-cyclohexanone (796 mg, 3.0 mmol) and 2-benzofuran-3-yl-ethanol (487 mg, 3.0 mmol) were dissolved in dichloromethane, and trifluoromethanesulfonic acid trimethylsilyl ester (0.59 ml, 3.06 mmol) was added thereto at RT. Stirring was carried out for 90 minutes at room temperature, and then 15 ml of 1M sodium hydroxide solution were added and stirring was continued for a further 30 minutes. The phases were separated and the aqueous phase was extracted with dichloromethane. After concentration of the solvent by evaporation, the crude product was obtained in a yield of 1.2 g (95%).

1,1-(2-(Dimethylaminomethyl)-3-hydroxy-3-(3-fluorophenyl)-pentamethylene)-1,3,4,9-tetrahydro-pyrano[3,4-b]benzofuran citrate

Example 8

1,1-(2-(Dimethylaminomethyl)-3-hydroxy-3-(3-fluorophenyl)-pentamethylene)-1,3,4,9-tetrahydro-pyrano[3,4-b]benzofuran (1.2 g, 1.9 mmol) was dissolved in 8 ml of ethanol, and 563 mg of citric acid were added thereto. After 18 hours' stirring at RT, the solution was concentrated. The product was obtained in the form of a colorless foam (1.7 g, 2.8 mmol, 97%).

1,1-(2-(Dimethylaminomethyl)-3-hydroxy-3-phenyl-pentamethylene)-1,3,4,9-tetrahydro-2-thia-9-azafluorene 3-Dimethylaminomethyl-4-phenyl-4-hydroxy-cyclohexanone (1.4 g, 5.7 mmol) and 2-(1H-indol-3-yl)-ethanethiol (1.0 g, 5.7 mmol) were dissolved in 26 ml of glacial acetic acid. 6 ml of phosphoric acid were added dropwise at about 10° C., and stirring was carried out for 24 hours at RT. 190 ml of 1M sodium hydroxide solution and 150 ml of dichloromethane were added at 0° C., and stirring was carried out for 30 minutes at RT. The phases were separated and the aqueous phase was extracted with dichloromethane. After concentration of the solvent, 1.35 g (59%) of the crude product were obtained.

1,1-(2-(Dimethylaminomethyl)-3-hydroxy-3-phenyl-pentamethylene)-1,3,4,9-tetrahydro-2-thia-9-azafluorene citrate

Example 9

1,1-(2-(Dimethylaminomethyl)-3-hydroxy-3-phenyl-pentamethylene)-1,3,4,9-tetrahydro-2-thia-9-aza-fluorene (1.35 g, 3.3 mmol) was dissolved in 4 ml of ethanol, and citric acid (640 mg, 3.3 mmol) was added thereto. Concentration yielded the product in the form of a colorless foam (1.82 g, 92%).

1,1-(2-(Dimethylaminomethyl)-3-hydroxy-3-(3-fluorophenyl)-pentamethylene)-1,3,4,9-tetrahydro-pyrano[3,4-b]benzothiophene 3-Dimethylaminomethyl-4-(3-fluorophenyl)-4-hydroxy-cyclohexanone (796 mg, 3.0 mmol) and 2-benzo[b]thiophen-3-yl-ethanol (535 mg, 3.0 mmol) were dissolved in dichloromethane, and trifluoromethanesulfonic acid trimethylsilyl ester (0.59 ml, 3.06 mmol) was added thereto at RT. After 2 hours at RT, 15 ml of 1M sodium hydroxide solution were added and stirring was carried out for 30 minutes. The phases were separated and extraction was carried out with dichloromethane. After concentration, chromatography was carried out on silica gel (eluant: dichloromethane/methanol 19:1) and the product was obtained in the form of a colorless foam (700 mg, 57%).

1,1-(2-(Dimethylaminomethyl)-3-hydroxy-3-(3-fluorophenyl)-pentamethylene)-1,3,4,9-tetrahydro-pyrano[3,4-b]benzothiophene citrate Example 10

1,1-(2-(Dimethylaminomethyl)-3-hydroxy-3-(3-fluorophenyl)-pentamethylene)-1,3,4,9-tetrahydro-pyrano[3,4-b]benzothiophene (700 mg, 1.7 mmol) was dissolved in 5 ml of ethanol, and citric acid (326 mg) was added thereto. Stirring was carried out for 16 hours at RT. Concentration yielded a colorless foam (1.05 g, 99%).

1,1-(2-(Dimethylaminomethyl)-3-hydroxy-3-(2-methylphenyl)-pentamethylene)-1,3,4,9-tetrahydro-pyrano[3,4-b]benzothiophene 3-Dimethylaminomethyl-4-(2-methylphenyl)-4-hydroxy-cyclohexanone (653 mg, 2.5 mmol) and 2-benzo[b]thiophen-3-yl-ethanol (450 mg, 2.5 mmol) were dissolved in dichloromethane, and trifluoromethanesulfonic acid trimethylsilyl ester (0.48 ml, 2.6 mmol) was added thereto at RT. After 2 hours' stirring at RT, 15 ml of 1M sodium hydroxide solution were added and stirring was continued for a further 30 minutes. The phases were separated and the aqueous phase was extracted with dichloromethane. The crude product was chromatographed on silica gel (eluant: dichloromethane/methanol 9:1). The desired product was obtained in the form of a yellowish solid (900 mg, 85%).

1,1-(2-(Dimethylaminomethyl)-3-hydroxy-3-(2-methylphenyl)-pentamethylene)-1,3,4,9-tetrahydro-pyrano[3,4-b]benzothiophene citrate Example 11

1,1-(2-(Dimethylaminomethyl)-3-hydroxy-3-(2-methylphenyl)-pentamethylene)-1,3,4,9-tetrahydro-pyrano[3,4-b]benzothiophene (900 mg, 2.13 mmol) was dissolved in 5 ml of ethanol; citric acid (410 mg) was added thereto, and stirring was carried out for 16 hours at RT. After concentration, a colorless solid was obtained (1.2 g, 92%).

1,1-(2-(Dimethylaminomethyl)-3-hydroxy-3-(2-methylphenyl)-pentamethylene)-1,3,4,9-tetrahydro-pyrano[3,4-b]benzofuran 3-Dimethylaminomethyl-4-(2-methylphenyl)-4-hydroxy-cyclohexanone (784 mg, 3.0 mmol) and 2-benzofuran-3-yl-ethanol (487 mg, 3.0 mmol) were dissolved in dichloromethane, and trifluoromethanesulfonic acid trimethylsilyl ester (0.59 ml, 3.06 mmol) was added at RT. After 2 hours' stirring at RT, 15 ml of 1M sodium hydroxide solution were added and stirring was continued for a further 30 minutes. The phases were separated and the aqueous phase was extracted with dichloromethane. The crude product was chromatographed on silica gel (eluant: dichloromethane/methanol 9:1). The desired product was obtained in the form of a yellowish foam (760 mg, 62%).

1,1-(2-(Dimethylaminomethyl)-3-hydroxy-3-(2-methylphenyl)-pentamethylene)-1,3,4,9-tetrahydro-pyrano[3,4-b]benzofuran citrate Example 12

1,1-(2-(Dimethylaminomethyl)-3-hydroxy-3-(2-methylphenyl)-pentamethylene)-1,3,4,9-tetrahydro-pyrano[3,4-b]benzofuran (760 mg, 1.9 mmol) was dissolved in 5 ml of ethanol; citric acid (360 mg) was added, and stirring was carried out for 16 hours at RT. After concentration, a colorless foam was obtained (1.0 g, 88%).

1,1-(2-(Dimethylaminomethyl)-3-hydroxy-3-(4-trifluoro-methylphenyl)-pentamethylene)-1,3,4,9-tetrahydro-pyrano[3,4-b]benzofuran 3-Dimethylaminomethyl-4-(4-trifluoromethylphenyl)-4-hydroxy-cyclohexanone (946 mg, 3.0 mmol) and 2-benzofuran-3-yl-ethanol (487 mg, 3.0 mmol) were dissolved in dichloromethane, and trifluoromethanesulfonic acid trimethylsilyl ester (0.59 ml, 3.06 mmol) was added at RT. After 2 hours' stirring at RT, 15 ml of 1M sodium hydroxide solution were added and stirring was continued for a further 30 minutes. The phases were separated and the aqueous phase was extracted with dichloromethane. The crude product was chromatographed on silica gel (eluant: dichloromethane/methanol 9:1). The desired product was obtained in the form of a yellowish foam (560 mg, 41%).

1,1-(2-(Dimethylaminomethyl)-3-hydroxy-3-(4-trifluoro-methylphenyl)-pentamethylene)-1,3,4,9-tetrahydro-pyrano[3,4-b]benzofuran citrate Example 13

1,1-(2-(Dimethylaminomethyl)-3-hydroxy-3-(4-trifluoromethyl-phenyl)-pentamethylene)-1,3,4,9-tetrahydro-pyrano[3,4-b]benzofuran (560 mg, 1.22 mmol) was dissolved in 5 ml of ethanol; citric acid (234 mg) was added thereto, and stirring was carried out for 16 hours at room temperature. After concentration, a colorless foam was obtained (785 mg, 99%).

1,1-(2-(Dimethylaminomethyl)-3-hydroxy-3-(3-fluorophenyl)-pentamethylene)-1,3,4,9-tetrahydro-2-thia-9-aza-fluorene 3-Dimethylaminomethyl-4-(3-fluorophenyl)-4-hydroxy-cyclohexanone (1.0 g, 3.8 mmol) and 2-(1H-indol-3-yl)-ethanethiol (670 mg, 3.8 mmol) were dissolved in 17 ml of glacial acetic acid. 4 ml of phosphoric acid were added dropwise at 5° C., and stirring was carried out for 24 hours at RT. 130 ml of 1M sodium hydroxide solution and 100 ml of dichloromethane were added at 5° C., and stirring was carried out for 2 hours at RT. The phases were separated and the aqueous phase was extracted with dichloromethane. After concentration of the solvent, 839 mg (52%) of the crude product were obtained.

1,1-(2-(Dimethylaminomethyl)-3-hydroxy-3-(3-fluorophenyl)-pentamethylene)-1,3,4,9-tetrahydro-2-thia-9-aza-fluorene citrate Example 14

1,1-(2-(Dimethylaminomethyl)-3-hydroxy-3-(3-fluorophenyl)-pentamethylene)-1,3,4,9-tetrahydro-2-thia-9-aza-fluorene (839 mg, 1.98 mmol) was dissolved in 3 ml of ethanol, and citric acid (380 mg, 2.0 mmol) was added thereto. The product was obtained in the form of a colorless solid (1.26 g, 97%).

1,1-(2-(Dimethylaminomethyl)-3-hydroxy-3-(4-trifluoromethyl-phenyl)-pentamethylene)-3,4-dihydro-1H-2,9-diazafluorene 3-Dimethylaminomethyl-4-(4-trifluoromethyl-phenyl)-4-hydroxy-cyclohexanone (1.26 g, 4.0 mmol) and tryptamine (640 mg, 4.0 mmol) were dissolved in 26 ml of methanol; 1.28 g of sodium sulfate were added, and stirring was carried out for 2 hours at RT. After removal of the solvent by distillation, the residue was taken up in 26 ml of 1,2-dichloroethane. Trifluoroacetic acid (3.2 ml) was added at 0° C. and stirring was carried out for 24 hours at RT. 26 ml of water were added at 0° C. and the pH was adjusted to 11 with 5M sodium hydroxide solution. After phase separation, the aqueous phase was extracted with 1,2-dichloroethane. 364 mg (22%) of the crude product were obtained.

1,1-(2-(Dimethylaminomethyl)-3-hydroxy-3-(4-trifluoromethylphenyl)-pentamethylene)-3,4-dihydro-1H-2,9-diazafluorene dicitrate Example 15

1,1-(2-(Dimethylaminomethyl)-3-hydroxy-3-(4-trifluoromethylphenyl)-pentamethylene)-3,4-dihydro-1H-2,9-diazafluorene (364 mg, 0.9 mmol) was dissolved in 4 ml of ethanol, and citric acid (166 mg, 0.9 mmol) was added thereto. The product was obtained in the form of a colorless precipitate (356 mg, 47%).

1,1-(2-(Dimethylaminomethyl)-3-hydroxy-3-(3-fluorophenyl)-pentamethylene)-7-fluoro-3,4-dihydro-1H-2,9-diazafluorene 3-Dimethylaminomethyl-4-(3-fluoro-phenyl)-4-hydroxy-cyclohexanone (1.1 g, 4.1 mmol) and tryptamine (740 mg, 4.1 mmol) were dissolved in 33 ml of methanol; 1.64 g of sodium sulfate were added, and stirring was carried out for one hour at RT. After removal of the solvent by distillation, the residue was taken up in 30 ml of 1,2-dichloroethane. Trifluoroacetic acid (3.28 ml) was added at 0° C. and stirring was carried out for 24 hours at RT. 30 ml of water were added at 0° C. and the pH was adjusted to 11 with 5M sodium hydroxide solution. After phase separation, the aqueous phase was extracted with 1,2-dichloroethane. The crude product was chromatographed on silica gel (eluant: EE/methanol 4:1), and the product was obtained in a yield of 89 mg (5%).

1,1-(2-(Dimethylaminomethyl)-3-hydroxy-3-(3-fluorophenyl)-pentamethylene)-7-fluoro-3,4-dihydro-1H-2,9-diazafluorene sesquicitrate Example 16

1,1-(2-(Dimethylaminomethyl)-3-hydroxy-3-(3-fluorophenyl)-pentamethylene)-7-fluoro-3,4-dihydro-1H-2,9-diazafluorene (89 mg, 0.2 mmol) was dissolved in 3 ml of ethanol, and citric acid (40 mg, 0.21 mmol) was added thereto. The product was obtained in the form of a colorless precipitate (66 mg, 46%).

1,1-(2-(Dimethylaminomethyl)-3-hydroxy-3-phenyl-pentamethylene)-3,4-dihydro-6-methoxy-1H-2,9-diazafluorene 3-Dimethylaminomethyl-4-phenyl-4-hydroxy-cyclohexanone (980 mg, 4.0 mmol) and tryptamine (740 mg, 4.1 mmol) were dissolved in 33 ml of methanol; 1.6 g of sodium sulfate were added, and stirring was carried out for one hour at RT. After removal of the solvent by distillation, the residue was taken up in 30 ml of 1,2-dichloroethane. Trifluoroacetic acid (3.2 ml) was added at 0° C. and stirring was carried out for 24 hours at RT. 30 ml of water were added at 0° C. and the pH was adjusted to 11 with 5M sodium hydroxide solution. After phase separation, the aqueous phase was extracted with 1,2-dichloroethane. The crude product was chromatographed on silica gel (eluant: ether with 1% 25% ammonia solution), and the product was obtained in a yield of 575 mg (33%).

1,1-(2-(Dimethylaminomethyl)-3-hydroxy-3-phenyl-pentamethylene)-3,4-dihydro-6-methoxy-1H-2,9-diazafluorene citrate Example 17

1,1-(2-(Dimethylaminomethyl)-3-hydroxy-3-phenyl-pentamethylene)-3,4-dihydro-6-methoxy-1H-2,9-diazafluorene (575 mg, 1.3 mmol) was dissolved in 10 ml of ethanol, and citric acid (255 mg, 1.33 mmol) was added thereto. The product was obtained in the form of a colorless precipitate (586 mg, 96%).

1,1-(2-(Dimethylaminomethyl)-3-hydroxy-3-(4-methylthiophenyl)-pentamethylene)-1,3,4,9-tetrahydro-6-methoxy-pyrano[3,4-b]indole 3-Dimethylaminomethyl-4-(4-methylthiophenyl)-4-hydroxy-cyclohexanone (733 mg, 2.5 mmol) and 5-methoxy-tryptamine (475 mg, 2.5 mmol) were dissolved in 20 ml of methanol; 1.0 g (7 mmol) of sodium sulfate were added, and stirring was carried out for one hour at RT. After removal of the solvent by distillation, the residue was taken up in 20 ml of 1,2-dichloroethane. Trifluoroacetic acid (2.0 ml, 26 mmol) was added at 0° C. and stirring was carried out for 24 hours at RT. 20 ml of water were added and the pH was adjusted to 11 with 5M sodium hydroxide solution. After phase separation, the aqueous phase was extracted with 1,2-dichloroethane. The crude product was chromatographed on silica gel (eluant: dichloromethane/methanol 9:1), and the product was obtained in a yield of 740 mg (63%).

1,1-(2-(Dimethylaminomethyl)-3-hydroxy-3-(4-methylthiophenyl)-pentamethylene)-1,3,4,9-tetrahydro-6-methoxy-pyrano[3,4-b]indole citrate Example 18

1,1-(2-(Dimethylaminomethyl)-3-hydroxy-3-(4-methylthiophenyl)-pentamethylene)-1,3,4,9-tetrahydro-6-methoxy-pyrano[3,4-b]indole (520 mg, 1.11 mmol) was dissolved in 15 ml of ethanol, and citric acid (219 mg) was added thereto. The product was obtained in the form of a colorless precipitate (670 mg, 92%).

1,1-(2-(Dimethylaminomethyl)-3-hydroxy-3-(2-methylphenyl)-pentamethylene)-1,3,4,9-tetrahydro-6-methoxy-pyrano[3,4-b]indole 3-Dimethylaminomethyl-4-(2-methylphenyl)-4-hydroxy-cyclohexanone (653 mg, 2.5 mmol) and 5-methoxytryptamine (475 mg, 2.5 mmol) were dissolved in 20 ml of methanol; 1.0 g (7 mmol) of sodium sulfate were added, and stirring was carried out for one hour at RT. After removal of the solvent by distillation, the residue was taken up in 20 ml of 1,2-dichloroethane. Trifluoroacetic acid (2.0 ml, 26 mmol) was added at RT and stirring was carried out for 24 hours at RT. 20 ml of water were added and the pH was adjusted to 11 with 5M sodium hydroxide solution. After phase separation, the aqueous phase was extracted with 1,2-dichloroethane. The crude product was chromatographed on silica gel (eluant: dichloromethane/methanol 9:1), and the product was obtained in a yield of 800 mg (74%).

1,1-(2-(Dimethylaminomethyl)-3-hydroxy-3-(2-methylphenyl)-pentamethylene)-1,3,4,9-tetrahydro-6-methoxy-pyrano[3,4-b]indole citrate Example 19

1,1-(2-(Dimethylaminomethyl)-3-hydroxy-3-(2-methylphenyl)-pentamethylene)-1,3,4,9-tetrahydro-6-methoxy-pyrano[3,4-b]indole (550 mg, 1.27 mmol) was dissolved in 5 ml of ethanol, and citric acid (235 mg) was added thereto. The product was obtained in the form of a colorless precipitate (580 mg, 73%).

1,1-(2-(Dimethylaminomethyl)-3-hydroxy-3-(4-methylthiophenyl)-pentamethylene)-1,3,4,9-tetrahydro-pyrano[3,4-b]indole 3-Dimethylaminomethyl-4-(4-methylthio-phenyl)-4-hydroxy-cyclohexanone (1.2 g, 4.1 mmol) and tryptophol (660 mg, 4.1 mmol) were dissolved in 40 ml of dichloromethane, and trifluoromethanesulfonic acid trimethylsilyl ester (3.69 ml, 20.4 mmol) were added thereto at 0° C. Stirring was carried out for 24 hours at RT and then 30 ml of water were added and the pH was adjusted to 11 with 1M sodium hydroxide solution. The phases were separated and the aqueous phase was extracted with dichloromethane. The crude product was chromatographed on silica gel (eluant: EE/methanol 9:1). 270 mg (0.62 mmol, 15%) of the product were obtained.

1,1-(2-(Dimethylaminomethyl)-3-hydroxy-3-(4-methylthiophenyl)-pentamethylene)-1,3,4,9-tetrahydro-pyrano[3,4-b]indole citrate Example 20

1,1-(2-(Dimethylaminomethyl)-3-hydroxy-3-(4-methylthiophenyl)-pentamethylene)-1,3,4,9-tetrahydro-pyrano[3,4-b]indole (270 mg, 0.62 mmol) was suspended in 10 ml of ethanol, and citric acid (119 mg, 0.62 mmol) was added thereto. After concentration of the solvent by evaporation, the product was obtained in the form of a colorless foam (411 mg, 65%).

1,1-(2-(Dimethylaminomethyl)-3-hydroxy-3-(3-fluorophenyl)-pentamethylene)-3,4-dihydro-6-methoxy-1H-2,9-diazafluorene 3-Dimethylaminomethyl-4-(3-fluorophenyl)-4-hydroxy-cyclohexanone (663 mg, 2.5 mmol) and 5-methoxytryptamine (475 mg, 2.5 mmol) were dissolved in 20 ml of methanol; 1.0 g of sodium sulfate was added and stirring was carried out for one hour at RT. After removal of the solvent by distillation, the residue was suspended in 20 ml of 1,2-dichloroethane; trifluoroacetic acid (2.0 ml, 26 mmol) was added at RT, and stirring was carried out for 3 hours. 20 ml of water were then added to the mixture, the pH was adjusted to 11 with sodium hydroxide solution, and the aqueous phase was extracted with 1,2-dichloroethane. The crude product was chromatographed on silica gel (eluant: ether with 2% 25% ammonia). 395 mg (36%) of the product were obtained.

1,1-(2-(Dimethylaminomethyl)-3-hydroxy-3-(3-fluorophenyl)-pentamethylene)-3,4-dihydro-6-methoxy-1H-2,9-diazafluorene citrate Example 21

1,1-(2-(Dimethylaminomethyl)-3-hydroxy-3-(3-fluorophenyl)-pentamethylene)-3,4-dihydro-6-methoxy-1H-2,9-diazafluorene (395 mg, 0.9 mmol) was dissolved at 70° C. in 5 ml of ethanol, and citric acid (173 mg) was added thereto. After cooling, the product was obtained in the form of a colorless precipitate (315 mg, 56%).

1,1-(2-(Dimethylaminomethyl)-3-hydroxy-3-(4-trifluoro-methylphenyl)-pentamethylene)-3,4-dihydro-6-methoxy-1H-2,9-diazafluorene 3-Dimethylaminomethyl-4-(4-trifluoromethylphenyl)-4-hydroxy-cyclohexanone (788 mg, 2.5 mmol) and 5-methoxytryptamine (475 mg, 2.5 mmol) were dissolved in 20 ml of methanol; 1.0 g of sodium sulfate was added and stirring was carried out for 3 hours at RT. After removal of the solvent by distillation, the residue was suspended in 20 ml of 1,2-dichloroethane; trifluoroacetic acid (2.0 ml, 26 mmol) was added at RT, and stirring was carried out for 3 hours. 20 ml of water were then added to the mixture, the pH was adjusted to 11 with sodium hydroxide solution, and the aqueous phase was extracted with 1,2-dichloroethane. The crude product was chromatographed on silica gel (eluant: ether with 2% 25% ammonia). 717 mg (66%) of the product were obtained.

1,1-(2-(Dimethylaminomethyl)-3-hydroxy-3-(4-trifluoromethylphenyl)-pentamethylene)-3,4-dihydro-6-methoxy-1H-2,9-diazafluorene citrate Example 22

1,1-(2-(Dimethylaminomethyl)-3-hydroxy-3-(4-trifluoromethylphenyl)-pentamethylene)-3,4-dihydro-6-methoxy-1H-2,9-diazafluorene (717 mg, 1.47 mmol) was dissolved at 50° C. in 5 ml of ethanol, and citric acid (282 mg) was added thereto. After cooling, the product was obtained in the form of a colorless precipitate (860 mg, 86%).

1,1-(2-(Dimethylaminomethyl)-3-hydroxy-3-(4-methylthiophenyl)-pentamethylene)-1,3,4,9-tetrahydro-2-thia-9-aza-fluorene 3-Dimethylaminomethyl-4-(4-methylthio-phenyl)-4-hydroxy-cyclohexanone (1.0 g, 3.4 mmol) and 2-(1H-indol-3-yl)-ethanethiol (604 mg, 3.4 mmol) were dissolved in 15 ml of glacial acetic acid. 4 ml of 85% phosphoric acid were added dropwise at 10° C. and stirring was carried out for 20 hours at RT. 96 ml of dichloromethane were added at 10° C., the pH was adjusted to 9 with 5M sodium hydroxide solution, and stirring was then carried out for one hour. The phases were separated and the aqueous phase was extracted with dichloromethane. After removal of the solvent by distillation, the crude product was obtained in a yield of 964 mg (63%).

1,1-(2-(Dimethylaminomethyl)-3-hydroxy-3-(4-methylthiophenyl)-pentamethylene)-1,3,4,9-tetrahydro-2-thia-9-aza-fluorene sesquicitrate

Example 23

1,1-(2-(Dimethylaminomethyl)-3-hydroxy-3-(4-methylthiophenyl)-pentamethylene)-1,3,4,9-tetrahydro-2-thia-9-aza-fluorene (710 mg, 1.57 mmol) was dissolved in. 10 ml of ethanol at boiling heat. Citric acid (1.57 mmol) was added thereto. After concentration, the product was obtained in the form of a yellowish foam in a yield of 779 mg (67%).

1,1-(2-(Dimethylaminomethyl)-3-hydroxy-3-(2-methylphenyl)-pentamethylene)-1,3,4,9-tetrahydro-2-thia-9-aza-fluorene 3-Dimethylaminomethyl-4-(2-methylphenyl)-4-hydroxy-cyclohexanone (980 mg, 3.7 mmol) and 2-(1H-indol-3-yl)-ethanethiol (660 mg, 3.7 mmol) were dissolved in 17 ml of glacial acetic acid. 4 ml of 85% phosphoric acid were added dropwise at 5° C., and stirring was carried out for 20 hours at RT. 100 ml of dichloromethane were added at 5° C., the pH was adjusted to 9 with 5M sodium hydroxide solution, and then stirring was carried out for one hour. The phases were separated and the aqueous phase was extracted with dichloromethane. After removal of the solvent by distillation, the crude product was obtained in a yield of 541 mg (35%).

1,1-(2-(Dimethylaminomethyl)-3-hydroxy-3-(2-methylphenyl)-pentamethylene)-1,3,4,9-tetrahydro-2-thia-9-aza-fluorene citrate

Example 24

1,1-(2-(Dimethylaminomethyl)-3-hydroxy-3-(2-methylphenyl)-pentamethylene)-1,3,4,9-tetrahydro-2-thia-9-aza-fluorene (541 mg, 1.29 mmol) was dissolved in 5 ml of ethanol, and citric acid (219 mg) was added thereto. After concentration, the product was obtained in the form of a brownish foam in a yield of 677 mg (86%).

1,1-(2-(Dimethylaminomethyl)-3-hydroxy-3-(2-methylphenyl)-pentamethylene)-1,3,4,9-tetrahydro-pyrano[3,4-b]indole 3-Dimethylaminomethyl-4-(2-methylphenyl)-4-hydroxy-cyclohexanone (1.0 g, 3.8 mmol) and tryptophol (620 mg, 3.8 mmol) were dissolved in 38 ml of dichloromethane. Trifluoromethanesulfonic acid trimethylsilyl ester (3.46 ml, 19 mmol) was added at 0° C. and stirring was carried out for 24 hours at RT. While cooling with ice, 30 ml of water were added and the pH was adjusted to 11 with 1M sodium hydroxide solution. The phases were separated and extracted with dichloromethane. The crude product was chromatographed on silica gel (eluant: EE/hexane 1:2+1% 25% ammonia). The product was obtained in a yield of 190 mg (12%).

1,1-(2-(Dimethylaminomethyl)-3-hydroxy-3-(2-methylphenyl)-pentamethylene)-1,3,4,9-tetrahydro-pyrano[3,4-b]indole citrate

Example 25

1,1-(2-(Dimethylaminomethyl)-3-hydroxy-3-(2-methylphenyl)-pentamethylene)-1,3,4,9-tetrahydro-pyrano[3,4-b]indole (190 mg, 0.47 mmol) was dissolved in 4 ml of ethanol, and 90 mg of citric acid (0.47 mmol) were added thereto. After concentration, 280 mg (0.469 mmol, 99%) of the product were obtained.

1,1-(2-(Dimethylaminomethyl)-3-hydroxy-3-(4-methylthio-phenyl)-pentamethylene)-3,4-dihydro-1H-2,9-diazafluorene 3-Dimethylaminomethyl-4-(4-methylthio-phenyl)-4-hydroxy-cyclohexanone (180 mg, 0.6 mmol) and tryptamine (100 mg, 0.6 mmol) were dissolved in 10 ml of methanol; 240 mg of sodium sulfate were added and stirring was carried out; for 24 hours at RT. After removal of the solvent by distillation, the residue was suspended in 10 ml of 1,2-dichloroethane; trifluoroacetic acid (0.48 ml) was added at RT, and stirring was carried out for 24 hours. 5 ml of water were then added to the mixture, the pH was adjusted to 11 with sodium hydroxide solution, and the aqueous phase was extracted with 1,2-dichloroethane. The crude product was chromatographed on silica gel (eluant: ether with 0.3% 25% ammonia). 74 mg (28%) of the product were obtained.

1,1-(2-(Dimethylaminomethyl)-3-hydroxy-3-(4-methylthio-phenyl)-pentamethylene)-3,4-dihydro-1H-2,9-diazafluorene citrate

Example 26

1,1-(2-(Dimethylaminomethyl)-3-hydroxy-3-(4-methylthiophenyl)-pentamethylene)-3,4-dihydro-1H-2,9-diazafluorene (74 mg, 0.17 mmol) was dissolved in 2 ml of ethanol, and citric acid (38 mg, 0.2 mmol) was added thereto. The product was obtained in the form of a colorless precipitate (56 mg, 53%).

1,1-(2-(Dimethylaminomethyl)-3-hydroxy-3-(3-fluorophenyl)-pentamethylene)-1,3,4,9-tetrahydro-pyrano[3,4-b]indole 3-Dimethylaminomethyl-4-(3-fluorophenyl)-4-hydroxy-cyclohexanone (490 mg, 1.9 mmol) and tryptophol (300 mmol, 1.9 mmol) were dissolved in 17 ml of dichloromethane. At RT, methanesulfonic acid (0.24 ml, 3.7 mmol) was added dropwise and stirring was carried out for 24 hours. The pH was adjusted to 11 with 1M sodium hydroxide solution, the phases were separated, and the aqueous phase was extracted with dichloromethane. The crude product was obtained in a yield of 801 mg (107%).

1,1-(2-(Dimethylaminomethyl)-3-hydroxy-3-(3-fluorophenyl)-pentamethylene)-1,3,4,9-tetrahydro-pyrano[3,4-b]indole hydrochloride

Example 27

1,1-(2-(Dimethylaminomethyl)-3-hydroxy-3-(3-fluorophenyl)-pentamethylene)-1,3,4,9-tetrahydro-pyrano[3,4-b]indole (801 mg, 2.0 mmol) was dissolved in ethyl methyl ketone, and 19 µl of water and 273 µl of trimethylchlorosilane were added thereto. After addition of ether, the product was obtained in the form of a greyish precipitate (124 mg, 15%).

1,1-(2-(Dimethylaminomethyl)-3-hydroxy-3-phenyl-pentamethylene)-3,4-dihydro-1H-2,9-diazafluorene 3-Dimethylaminomethyl-4-phenyl-4-hydroxy-cyclohexanone (1.0 g, 4.0 mmol) and tryptamine (650 mg, 4.0 mmol)

were dissolved in 35 ml of methanol; 1.8 g of sodium sulfate were added thereto and stirring was carried out for 24 hours at RT. After removal of the solvent by distillation, the residue was suspended in 35 ml of 1,2-dichloroethane; trifluoroacetic acid (3.2 ml) was added at RT and stirring was carried out for 24 hours. 30 ml of water were then added to the mixture, the pH was adjusted to 11 with sodium hydroxide solution and the aqueous phase was extracted with 1,2-dichloroethane. The crude product was chromatographed on silica gel (eluant: EE with 1% 25% ammonia). When the mixture was taken up in EE, a portion of the product remained behind as a precipitate. 80 mg (5%) of the product were obtained in this manner.

1,1-(2-(Dimethylaminomethyl)-3-hydroxy-3-phenyl-pentamethylene)-3,4-dihydro-1H-2,9-diazafluorene citrate Example 28

1,1-(2-(Dimethylaminomethyl)-3-hydroxy-3-phenyl-pentamethylene)-3,4-dihydro-1H-2,9-diazafluorene (80 mg, 0.2 mmol) was dissolved in 3 ml of ethanol, and citric acid (38 mg, 0.2 mmol) was added thereto. The product was obtained in the form of a colorless precipitate (104 mg, 91%).

Examples 29 to 31 were prepared analogously to Example 7 and Examples 32 to 35 analogously to Example 6.

| Example number | Structure (as base) | Name |
| --- | --- | --- |
| 1 | | 1,1-(2-(Dimethylaminomethyl)-3-hydroxy-3-(3-methoxyphenyl)pentamethylene)-3,4-dihydro-1H-2,9-diazafluorene dihydrochloride |
| 2 | | 1,1-(2-(Dimethylaminomethyl)-3-hydroxy-3-(3-methoxyphenyl)pentamethylene)-2-acetyl-3,4-dihydro-1H-2,9-diazafluorene hydrochloride |
| 3 | | 1,1-(2-(Dimethylaminomethyl)-3-hydroxy-3-(3-fluorophenyl)-pentamethylene)-3,4-dihydro-1H-2,9-diazafluorene citrate |

-continued

| Example number | Structure (as base) | Name |
|---|---|---|
| 4 | | 1,1-(2-(Dimethylaminomethyl)-3-hydroxy-3-phenyl-pentamethylene)-1,3,4,9-tetrahydro-pyrano[3,4-b]indole sesquicitrate |
| 5 | | 1,1-(2-(Dimethylaminomethyl)-3-hydroxy-3-phenyl-pentamethylene)-1,3,4,9-tetrahydro-pyrano[3,4-b]benzofuran citrate |
| 6 | | 1,1-(2-(Dimethylaminomethyl)-3-hydroxy-3-(2-methylphenyl)-pentamethylene)-3,4-dihydro-1H-2,9-diazafluorene citrate |
| 7 | | 1,1-(2-(Dimethylaminomethyl)-3-hydroxy-3-phenyl-pentamethylene)-1,3,4,9-tetrahydro-pyrano[3,4-b]benzothiophene citrate |
| 8 | | 1,1-(2-(Dimethylaminomethyl)-3-hydroxy-3-(3-fluorophenyl)-pentamethylene)-1,3,4,9-tetrahydro-pyrano[3,4-b]benzofuran citrate |

| Example number | Structure (as base) | Name |
|---|---|---|
| 9 | | 1,1-(2-(Dimethylaminomethyl)-3-hydroxy-3-phenyl-pentamethylene)-1,3,4,9-tetrahydro-2-thia-9-aza-fluorene citrate |
| 10 | | 1,1-(2-(Dimethylaminomethyl)-3-hydroxy-3-(3-fluorophenyl)-pentamethylene)-1,3,4,9-tetrahydro-pyrano[3,4-b]benzothiophene citrate |
| 11 | | 1,1-(2-(Dimethylaminomethyl)-3-hydroxy-3-(2-methylphenyl)-pentamethylene)-1,3,4,9-tetrahydro-pyrano[3,4-b]benzothiophene citrate |
| 12 | | 1,1-(2-(Dimethylaminomethyl)-3-hydroxy-3-(2-methylphenyl)-pentamethylene)-1,3,4,9-tetrahydro-pyrano[3,4-b]benzofuran citrate |
| 13 | | 1,1-(2-(Dimethylaminomethyl)-3-hydroxy-3-(4-trifluoromethylphenyl)-pentamethylene)-1,3,4,9-tetrahydro-pyrano[3,4-b]benzofuran citrate |

-continued

| Example number | Structure (as base) | Name |
|---|---|---|
| 14 | | 1,1-(2-(Dimethylaminomethyl)-3-hydroxy-3-(3-fluorophenyl)-pentamethylene)-1,3,4,9-tetrahydro-2-thia-9-aza-fluorene citrate |
| 15 | | 1,1-(2-(Dimethylaminomethyl)-3-hydroxy-3-(4-trifluoromethylphenyl)-pentamethylene)-3,4-dihydro-1H-2,9-diazafluorene dicitrate |
| 16 | | 1,1-(2-(Dimethylaminomethyl)-3-hydroxy-3-(3-fluorophenyl)-pentamethylene)-7-fluoro-3,4-dihydro-1H-2,9-diazafluorene sesquicitrate |
| 17 | | 1,1-(2-(Dimethylaminomethyl)-3-hydroxy-3-phenyl-pentamethylene)-3,4-dihydro-6-methoxy-1H-2,9-diazafluorene citrate |

-continued

| Example number | Structure (as base) | Name |
|---|---|---|
| 18 | | 1,1-(2-(Dimethylaminomethyl)-3-hydroxy-3-(4-methylthiophenyl)-pentamethylene)-1,3,4,9-tetrahydro-6-methoxy-pyrano[3,4-b]indole citrate |
| 19 | | 1,1-(2-(Dimethylaminomethyl)-3-hydroxy-3-(2-methylphenyl)-pentamethylene)-1,3,4,9-tetrahydro-6-methoxy-pyrano[3,4-b]indole citrate |
| 20 | | 1,1-(2-(Dimethylaminomethyl)-3-hydroxy-3-(4-methylthiophenyl)-pentamethylene)-1,3,4,9-tetrahydro-pyrano[3,4-b]indole citrate |
| 21 | | 1,1-(2-(Dimethylaminomethyl)-3-hydroxy-3-(3-fluorophenyl)-pentamethylene)-3,4-dihydro-6-methoxy-1H-2,9-diazafluorene citrate |

-continued

| Example number | Structure (as base) | Name |
|---|---|---|
| 22 | | 1,1-(2-(Dimethylaminomethyl)-3-hydroxy-3-(4-trifluoromethylphenyl)-pentamethylene)-3,4-dihydro-6-methoxy-1H-2,9-diazafluorene citrate |
| 23 | | 1,1-(2-(Dimethylaminomethyl)-3-hydroxy-3-(4-methylthiophenyl)-pentamethylene)-1,3,4,9-tetrahydro-2-thia-9-aza-fluorene sesquicitrate |
| 24 | | 1,1-(2-(Dimethylaminomethyl)-3-hydroxy-3-(2-methylphenyl)-pentamethylene)-1,3,4,9-tetrahydro-2-thia-9-aza-fluorene citrate |
| 25 | | 1,1-(2-(Dimethylaminomethyl)-3-hydroxy-3-(2-methylphenyl)-pentamethylene)-1,3,4,9-tetrahydro-pyrano[3,4-b]indole citrate |

-continued

| Example number | Structure (as base) | Name |
|---|---|---|
| 26 | | 1,1-(2-(Dimethylaminomethyl)-3-hydroxy-3-(4-methylthiophenyl)-pentamethylene)-3,4-dihydro-1H-2,9-diazafluorene citrate |
| 27 | | 1,1-(2-(Dimethylaminomethyl)-3-hydroxy-3-(3-fluorophenyl)-pentamethylene)-1,3,4,9-tetrahydro-pyrano[3,4-b]indole hydrochloride |
| 28 | | 1,1-(2-(Dimethylaminomethyl)-3-hydroxy-3-phenyl-pentamethylene)-3,4-dihydro-1H-2,9-diazafluorene citrate |
| 29 | | 1,1-(2-(Dimethylaminomethyl)-3-hydroxy-3-(4-trifluoromethylphenyl)-pentamethylene)-1,3,4,9-tetrahydro-pyrano[3,4-b]benzothiophene citrate |

| Example number | Structure (as base) | Name |
|---|---|---|
| 30 | | 1,1-(2-(Dimethylaminomethyl)-3-hydroxy-3-(4-methylthiophenyl)-pentamethylene)-1,3,4,9-tetrahydro-pyrano[3,4-b]benzofuran citrate |
| 31 | | 1,1-(2-(Dimethylaminomethyl)-3-hydroxy-3-(4-methylthiophenyl)-pentamethylene)-1,3,4,9-tetrahydro-pyrano[3,4-b]benzothiophene citrate |
| 32 | | 1,1-(2-(Dimethylaminomethyl)-3-hydroxy-3-(2-methylphenyl)-pentamethylene)-7-fluoro-3,4-dihydro-1H-2,9-diazafluorene citrate |
| 33 | | 1,1-(2-(Dimethylaminomethyl)-3-hydroxy-3-(4-trifluoromethylphenyl)-pentamethylene)-7-fluoro-3,4-dihydro-1H-2,9-diazafluorene citrate |
| 34 | | 1,1-(2-(Dimethylaminomethyl)-3-hydroxy-3-(4-methylthiophenyl)-pentamethylene)-7-fluoro-3,4-dihydro-1H-2,9-diazafluorene citrate |

-continued

| Example number | Structure (as base) | Name |
|---|---|---|
| 35 | | 1,1-(2-(Dimethylaminomethyl)-3-hydroxy-3-phenyl-pentamethylene)-7-fluoro-3,4-dihydro-1H-2,9-diazafluorene dicitrate |

Biological Testing a) Studies of Serotonin Reuptake Inhibition (5HT Uptake Inhibition)

In order to be able to carry out these in vitro studies, synaptosomes are freshly isolated from areas of rat brain. A so-called "$P_2$" fraction is used in each case, which is prepared according to the procedure of Gray and Whittaker (E. G. Gray and V. P. Whittaker (1962) J. Anat. 76, 79-88). For 5HT uptake, these vesicular particles are isolated from the hypothalamus of male rat brains. A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

b) Studies of Noradrenaline Reuptake Inhibition (NA Uptake Inhibition)

In order to be able to carry out these in vitro studies, synaptosomes are freshly isolated from areas of rat brain. A so-called "$P_2$" fraction is used in each case, which is prepared according to the procedure of Gray and Whittaker (E. G. Gray and V. P. Whittaker (1962) J. Anat. 76, 79-88). For NA uptake, these vesicular particles are isolated from the hypothalamus of male rat brains. A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

c) Measurement of μ Binding

The receptor affinity for the human μ-opiate receptor was determined in a homogeneous batch on microtitre plates. To that end, serial dilutions of the substituted spirocyclic cyclohexane derivative to be tested were incubated for 90 minutes at room temperature with a receptor membrane preparation (15-40 μg of protein per 250 μl of incubation batch) of CHO-K1 cells, which express the human μ-opiate receptor (RB-HOM receptor membrane preparation from NEN, Zaventem, Belgium), in the presence of 1 nmol/l of the radioactive ligand [$^3$H]-naloxone (NET719, NEN, Zaventem, Belgium) and 1 mg of WGA-SPA beads (wheatgerm agglutinin SPA beads from Amersham/Pharmacia, Freiburg, Germany) in a total volume of 250 μl. The incubation buffer used was 50 mmol/l of Tris-HCl supplemented with 0.05 wt. % sodium azide and with 0.06 wt. % bovine serum albumin. In order to determine non-specific binding, 25 μmol/l of naloxone were additionally added. When the ninety-minute incubation time was complete, the microtitre plates were centrifuged off for 20 minutes at 1000 g and the radioactivity was measured in a β-counter (Microbeta-Trilux, PerkinElmer Wallac, Freiburg, Germany). The percentage displacement of the radioactive ligand from its binding to the human μ-opiate receptor at a concentration of the test substances of 1 μmol/l was determined and stated as the percentage inhibition (% inhibition) of specific binding. In some cases, on the basis of the percentage displacement by different concentrations of the compounds of formula I to be tested, $IC_{50}$ inhibitory concentrations, which effect 50% displacement of the radioactive ligand, were calculated. Ki values for the test substances were obtained by conversion by means of the Cheng-Prusoff equation.

The following binding data were determined, by way of example:

| Example number | μ binding (%) [1 μM] |
|---|---|
| 1 | 40 |
| 2 | 65 |
| 4 | 74 |
| 5 | 58 |
| 8 | 73 |
| 12 | 56 |
| 27 | 64 |
| 28 | 57 |
| 34 | 54 |

| Example number | 5-HT uptake, % inhibition (10 μM) |
|---|---|
| 1 | 44 |
| 3 | 75 |
| 4 | 84 |
| 5 | 84 |
| 6 | 69 |
| 7 | 88 |
| 8 | 88 |

-continued

| Example number | 5-HT uptake, % inhibition (10 μM) |
|---|---|
| 9 | 81 |
| 10 | 88 |
| 11 | 85 |
| 12 | 68 |
| 13 | 60 |
| 14 | 61 |
| 15 | 83 |
| 16 | 72 |
| 17 | 57 |
| 20 | 58 |
| 21 | 57 |
| 22 | 47 |
| 23 | 50 |
| 24 | 75 |
| 27 | 83 |
| 29 | 47 |
| 30 | 83 |
| 31 | 82 |
| 32 | 75 |
| 33 | 78 |
| 34 | 65 |
| 35 | 67 |

| Example number | NA uptake % inhibition (10 μM) |
|---|---|
| 1 | 43 |
| 3 | 48 |
| 5 | 51 |
| 7 | 59 |
| 8 | 66 |
| 10 | 55 |
| 11 | 43 |
| 12 | 41 |
| 13 | 46 |
| 14 | 46 |
| 15 | 76 |
| 18 | 41 |
| 21 | 44 |
| 24 | 42 |
| 26 | 40 |
| 29 | 35 |
| 30 | 37 |
| 31 | 60 |
| 32 | 38 |
| 33 | 68 |
| 34 | 57 |

Parental Solution of a Spirocyclic Cyclohexane Derivative According to the Invention 38 g of one of the spirocyclic cyclohexane compounds according to the invention, in this case Example 1, are dissolved at room temperature in 1 litre of water for injection purposes and then adjusted to isotonic conditions by addition of anhydrous glucose for injection purposes.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A spirocyclic cyclohexane compound corresponding to formula I:

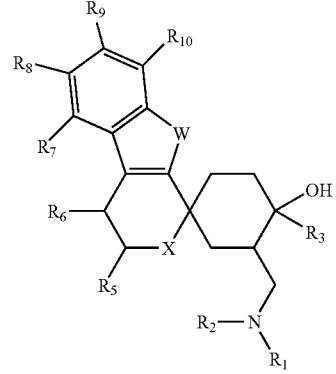

wherein $R^1$ and $R^2$ independently of one another represent H; CHO; $C_{1-5}$-alkyl, in each case saturated or unsaturated, branched or unbranched, mono- or poly-substituted or unsubstituted; or aryl, $C_{3-8}$-cycloalkyl or heteroaryl bonded via $C_{1-3}$-alkyl, in each case mono- or poly-substituted or unsubstituted; or $R^1$ and $R^2$ together represent $CH_2CH_2OCH_2CH_2$, $CH_2CH_2NR^{11}CH_2CH_2$ or $(CH_2)_{3-6}$, wherein $R^{11}$ represents H; $C_{1-5}$-alkyl, in each case saturated or unsaturated, branched or unbranched, mono- or poly-substituted or unsubstituted; $C_{3-8}$-cycloalkyl, in each case saturated or unsaturated, mono- or poly-substituted or unsubstituted; aryl or heteroaryl, in each case mono- or poly-substituted or unsubstituted; or aryl, $C_{3-8}$-cycloalkyl or heteroaryl bonded via $C_{1-3}$-alkyl, in each case mono- or poly-substituted or unsubstituted;

$R^3$ represents phenyl, phenethyl, thiophenyl, pyridyl or benzyl, in each case unsubstituted or mono- or poly-substituted;

W represents O or S;

$R^5$ represents $=O$; H; $COOR^{13}$, $CONR^{13}$, $OR^{13}$; $C_{1-5}$-alkyl, saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted;

$R^6$ represents H; F, Cl, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, saturated or unsaturated, branched or unbranched, unsubstituted or mono- or poly-substituted; $C_{3-8}$-cycloalkyl, saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted; or $R^5$ and $R^6$ together represent $(CH_2)_n$ wherein n=2, 3, 4, 5 or 6, wherein individual hydrogen atoms can also be replaced by F, Cl, Br, I, $NO_2$, $CF_3$, $OR^{13}$, CN or $C_{1-5}$-alkyl;

$R^7$, $R^8$, $R^9$ and $R^{10}$ independently of one another represent H, F, Cl, Br, I, $NO_2$, $CF_3$, $OR^{13}$, $SR^{13}$, $SO_2R^{13}$, $SO_2OR^{13}$, CN, $COOR^{13}$, $NR^{14}R^{15}$; $C_{1-5}$-alkyl, $C_{3-8}$-cycloalkyl, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted, wherein $R^{13}$ represents H; $C_{1-5}$-alkyl, in each case saturated or unsaturated, branched or unbranched, unsubstituted or mono- or poly-substituted; $C_{3-8}$-cycloalkyl, in each case saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted;

$R^{14}$ and $R^{15}$ independently of one another represent H; $C_{1-5}$-alkyl, in each case saturated or unsaturated, branched or unbranched, unsubstituted or mono- or poly-substituted; or $C_{3-8}$-cycloalkyl, in each case saturated or unsaturated, unsubstituted or mono- or poly-substituted; aryl or heteroaryl, unsubstituted or mono- or poly-substituted; or aryl, $C_{3-8}$-cycloalkyl or heteroaryl bonded via $C_{1-3}$-alkyl, unsubstituted or mono- or poly-substituted; or $R^{14}$ and $R^{15}$ together form $CH_2CH_2OCH_2CH_2$, $CH_2CH_2NR^{16}CH_2CH_2$ or $(CH_2)_{3-6}$, wherein
$R^{16}$ represents H; $C_{1-5}$-alkyl, saturated or unsaturated, branched or unbranched, unsubstituted or mono- or poly-substituted; and X represents O, S, SO, or $SO_2$;

or a pharmaceutically acceptable salt thereof;

in the form of a pure stereoisomer or a mixture of stereoisomers in any mixing ratio.

2. A compound according to claim 1, wherein said compound is present in the form of a pure enantiomer or diastereoisomer.

3. A compound according to claim 1, wherein said compound is present in the form of a racemic mixture.

4. A compound according to claim 1, wherein:
$R^1$ and $R^2$ independently of one another represent H; $C_{1-5}$-alkyl, saturated or unsaturated, branched or unbranched, mono- or poly-substituted or unsubstituted; or
$R^1$ and $R^2$ together form a ring and represent $CH_2CH_2OCH_2CH_2$, $CH_2CH_2NR^{11}CH_2CH_2$ or $(CH_2)_{3-6}$, wherein
$R^{11}$ represents H or $C_{1-5}$-alkyl, saturated or unsaturated, branched or unbranched, mono- or poly-substituted or unsubstituted.

5. A compound according to claim 1, wherein $R^1$ and $R^2$ independently of one another represent $CH_3$ or H, with the proviso that $R^1$ and $R^2$ do not simultaneously represent H.

6. A compound according to claim 1, wherein $R^3$ represents phenyl, unsubstituted or mono- or poly-substituted.

7. A compound according to claim 6, wherein $R^3$ represents unsubstituted phenyl or phenyl which is mono- or poly-substituted by at least one substituent selected from the group consisting of F, Cl, CN, $OCH_3$, $SCH_3$, $OCH_2CH_3$, $CH_3$, $CF_3$ and OH.

8. A compound according to claim 7, wherein $R^3$ represents phenyl, 3-methoxyphenyl, 2-methylphenyl, 4-trifluoromethylphenyl, 4-methylthiophenyl, 3-fluorophenyl or 4-fluorophenyl.

9. A compound according to claim 1, wherein X represents O or S.

10. A compound according to claim 1, wherein W represents O or S, and X represents O or S.

11. A compound according to claim 1, wherein $R^7$, $R^8$, $R^9$ and $R^{10}$ independently of one another represent H; $C_{1-5}$-alkyl, branched or unbranched, unsubstituted or mono- or poly-substituted; F, Cl, Br, I, $CF_3$, OH, $OCH_3$, $NH_2$, COOH, $COOCH_3$, $NHCH_3$, $N(CH_3)_2$ or $NO_2$.

12. A compound according to claim 11, wherein $R^7$, $R^8$, $R^9$ and $R^{10}$ independently of one another represent H, F or $OCH_3$.

13. A compound according to claim 1, wherein:
$R^5$ represents H, $C_{1-5}$-alkyl, branched or unbranched, unsubstituted or mono- or poly-substituted, or $COOR^{13}$, and
$R^6$ represents H or $C_{1-5}$-alkyl.

14. A compound according to claim 13, wherein $R^5$ and $R^6$ each represent H.

15. A compound according to claim 1, wherein $R^5$, $R^6$, $R^7$, $R^8$, $R^9$ and $R^{10}$ each represent H.

16. A compound according to claim 1, selected from the group consisting of:
1,1-(2-(dimethylaminomethyl)-3-hydroxy-3-phenyl-pentamethylene)-1,3,4,9-tetrahydro-pyrano[3,4-b]benzofuran citrate;
1,1-(2-(dimethylaminomethyl)-3-hydroxy-3-phenyl-pentamethylene)-1,3,4,9-tetrahydro-pyrano[3,4-b]benzothiophene citrate;
1,1-(2-(dimethylaminomethyl)-3-hydroxy-3-(3-fluorophenyl)-pentamethylene)-1,3,4,9-tetrahydro-pyrano[3,4-b]benzofuran citrate;
1,1-(2-(dimethylaminomethyl)-3-hydroxy-3-(3-fluorophenyl)-penta-methylene)-1,3,4,9-tetrahydro-pyrano[3,4-b]benzothiophene citrate;
1,1-(2-(dimethylaminomethyl)-3-hydroxy-3-(2-methylphenyl)-penta-methylene)-1,3,4,9-tetrahydro-pyrano[3,4-b]benzothiophene citrate;
1,1-(2-(dimethylaminomethyl)-3-hydroxy-3-(2-methylphenyl)-pentamethylene)-1,3,4,9-tetrahydro-pyrano[3,4-b]benzofuran citrate;
1,1-(2-(dimethylaminomethyl)-3-hydroxy-3-(4-trifluoromethylphenyl)-pentamethylene)-1,3,4,9-tetrahydro-pyrano[3,4-b]benzofuran citrate;
1,1-(2-(dimethylaminomethyl)-3-hydroxy-3-(4-trifluoromethylphenyl)-pentamethylene)-1,3,4,9-tetrahydro-pyrano[3,4-b]benzothiophene citrate;
1,1-(2-(dimethylaminomethyl)-3-hydroxy-3-(4-methylthiophenyl)-pentamethylene)-1,3,4,9-tetrahydro-pyrano[3,4-b]benzofuran citrate; and
1,1-(2-(dimethylaminomethyl)-3-hydroxy-3-(4-methylthiophenyl)-pentamethylene)-1,3,4,9-tetrahydro-pyrano[3,4-b]benzothiophene citrate;

or a free base thereof;

in the form of a pure stereoisomer or a mixture of stereoisomers in any mixing ratio.

17. A process for preparing a compound according to claim 1, said process comprising:
reacting a starting material of formula II

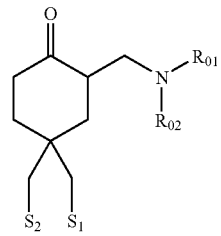

II wherein $R^{01}$ and $R^{02}$ independently have the meanings given for $R^1$ and $R^2$ or represent a protecting group,
in an organic solvent with an organometallic compound,
removing the ketal protecting group, and reacting the resulting product in the presence of a coupling reagent with a compound of formula B

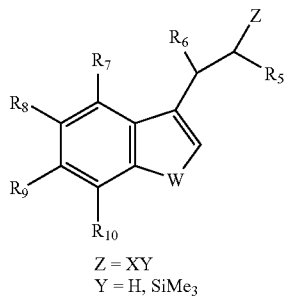

Z = XY
Y = H, SiMe$_3$ wherein X represents O or S.

18. A process according to claim 17, wherein said organometallic compounds is a Grignard compound of formula R$^3$MgX or an organolithium compound of formula R$^3$—Li.

19. A process according to claim 17, wherein the coupling reagent is selected from the group consisting of strong acids and silyl esters thereof.

20. A process for preparing a compound according to claim 1, wherein X represents SO or SO$_2$, said process comprising oxidizing a spirocyclic cyclohexane compound in which X represents S with an oxidizing agent.

21. A process according to claim 20, wherein said oxidizing agent is H$_2$O$_2$.

22. A pharmaceutical composition comprising a compound according to claim 1, and at least one pharmaceutically acceptable carrier or adjuvant.

* * * * *